United States Patent [19]

Wiedmann et al.

[11] Patent Number: 5,759,550

[45] Date of Patent: Jun. 2, 1998

[54] METHOD FOR SUPPRESSING XENOGRAFT REJECTION

[75] Inventors: Tien Wen Tao Wiedmann, Redwood City; Jian Wang, Palo Alto, both of Calif.

[73] Assignee: Pharmagenesis, Inc., Palo Alto, Calif.

[21] Appl. No.: 484,782

[22] Filed: Jun. 7, 1995

Related U.S. Application Data

[63] Continuation-in-part of Ser. No. 307,948, Sep. 15, 1994, abandoned, which is a continuation-in-part of Ser. No. 222,853, Apr. 5, 1994, abandoned, which is a continuation-in-part of Ser. No. 58,321, May 6, 1993, abandoned, and a continuation-in-part of Ser. No. 252,953, Jun. 2, 1994, abandoned.

[51] Int. Cl.$^6$ .................. A61K 35/78; A61K 31/56
[52] U.S. Cl. .................. 424/195.1; 514/164; 514/269; 514/468; 514/825; 514/861; 514/862; 514/863; 514/864; 514/881; 514/885; 514/887
[58] Field of Search ............ 424/195.1; 514/169, 514/269, 468, 825, 861–864, 881, 885, 887

[56] References Cited

U.S. PATENT DOCUMENTS

| 4,005,108 | 1/1977 | Kupchan et al. | 549/297 |
|---|---|---|---|
| 5,192,817 | 3/1993 | Takaishi et al. | 549/298 |
| 5,294,443 | 3/1994 | Lipisky et al. | 424/195.1 |

FOREIGN PATENT DOCUMENTS

| 89105432A | 12/1989 | China . |
|---|---|---|
| 3178-977-A | 9/1989 | Japan . |

OTHER PUBLICATIONS

Briggs, J.D., "A critical review of immunosuppressive therapy", Immunol. Let. 29:89–94,1, 1991.

Chen, K., et al., "Anti–AIDS Agents, 4. Tripterifordin, a Novel Anti–HIV Principle From *Tripterygium wilfordii:* Isolation and Structural Elucidation". J. Nat. Prod. 55(1):88–92, 1992.

Huying, S., et al., "Effects of *Tripterygium wilfordii* on the Menstruation of 50 Patients Suffering From Rheumatoid Arthritis—With a Summary of its Trerapeutic Effects in 12 Cases of Menorrhagia", JTrad. Chin. Med. 4(3):234–240, 1984.

Liao, C.X. et al., Antirejection Thereapy with *Tripterygium wolfordii* and Low–Dose Cyclosporin A in Small Bowel Transplantation in Pigs, Bull. Jinling Hosp. 6:265 (1992).

*Primary Examiner*—John W. Rollins
*Attorney, Agent, or Firm*—Vincent M. Powers; LeeAnn Gorthey

[57] ABSTRACT

An improved method for suppressing xenograft rejection in a host subject is disclosed. The method includes administering an immunosuppressant drug, where the drug or the amount of drug administered is, by itself, ineffective to suppress xenograft rejection. Effective xenograft suppression is achieved by also administering an ethanolic extract of *Triterygium wilfordii* or a purified triptolide component thereof.

10 Claims, 18 Drawing Sheets

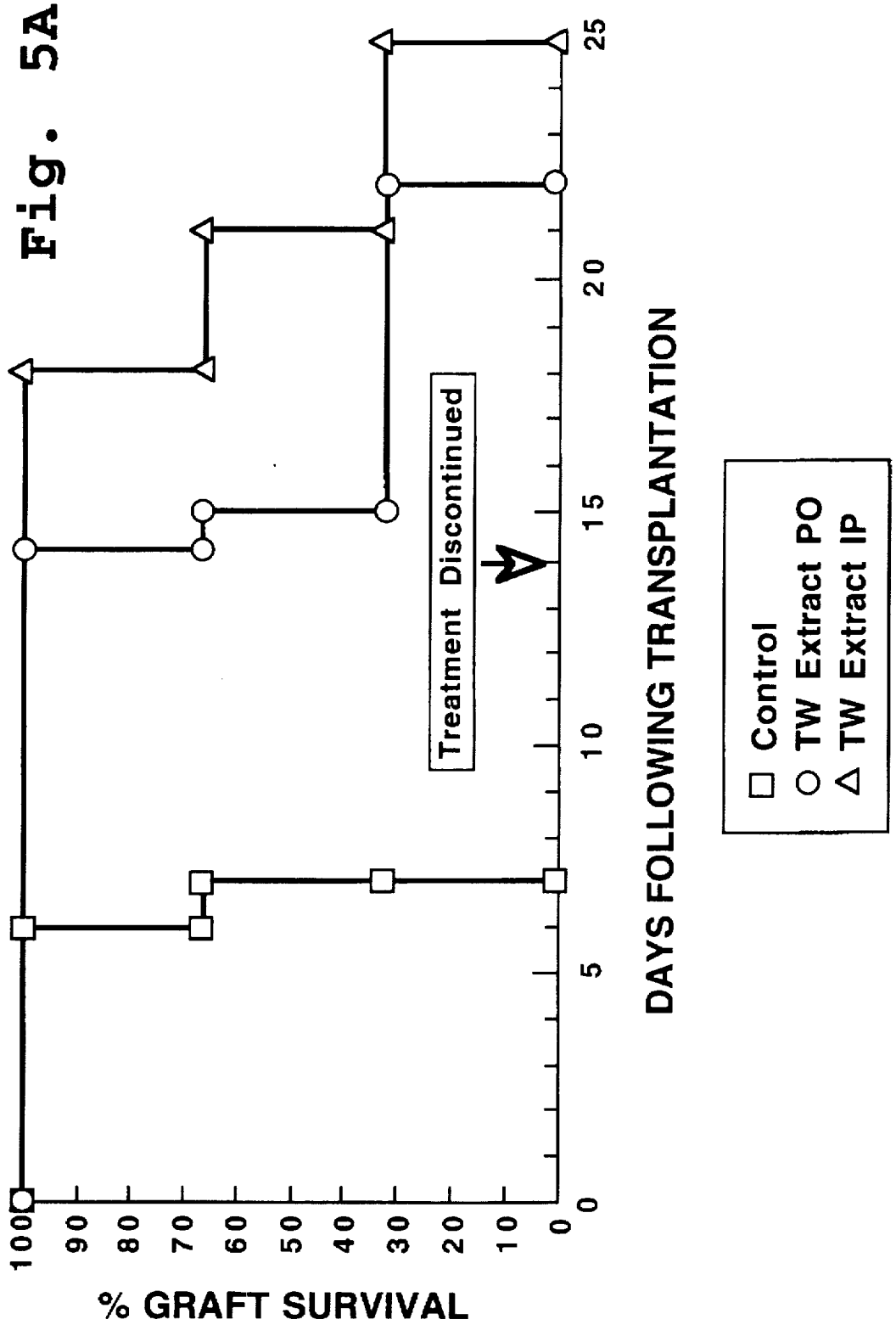

METHOD FOR SUPPRESSING XENOGRAFT REJECTION

This application is a continuation-in-part of Ser. No. 08/307,948 filed Sep. 15, 1994, now abandoned, which is a continuation-in-part of Ser. No. 08/222,853 filed Apr. 5, 1994, now abandoned, which is a continuation-in-part of Ser. No. 08/058,321 filed May 6, 1993; now abandoned, and a continuation-in-part of Ser. No. 08/252,953 filed Jun. 2, 1994, now abandoned all of which are incorporated herein by reference.

FIELD OF THE INVENTION

The present invention relates to a method for suppressing xenograft transplantation rejection in a host subject.

REFERENCES

Boyum., A., Scan J. Lab Invest. 21:77 (1968).

Bradley, L., In *Selected Methods in Cellular Immunology:* 162–164. W. H. Freeman and Company, San Francisco, 1980.

Briggs J. D., Immunology Letters Jul. 29(1–2):89–94 (1991).

Deng, F., et al., *Acta Pharm. Sin.* 17:146 (1982).

Deng, F., et al., *Acta Pharm. Sin.* 27:867 (1992).

Fidler, J. M., et al., Transplantation 55:367 (1993).

Gleichmann, e., et al., Immunol. Today 5:324 (1984).

Green, L. M., et al., J. Immunol Methods 70:257 (1984).

Hasan, R., et al., Transplantation 54:408 (1992).

Johnson, et al., *J. Chem. Soc.* 2884 (1963).

Kashiwada, Y., et al., *J. Nat. Prod.* 55:340 (1992).

Kennedy, M. S., et al., Am. J. Med. 78:978 (1983).

Keown, P. A., Ann. Rev. Trans., Clin. Transplants 205–223, (1991).

Korngold, R. and Sprent, J., J. Exp. Med. 148:1687 (1978).

Kupchan, S. M., et al., *J. Am. Chem. Soc.* 94:7194 (1972).

Kupchan, S. M., et al., U.S. Pat. No. 4,005,108 issued Jan. 25, 1977.

Mishell, B., et al., eds., *Selected Methods in Cellular Immunology*, Freeman and Co. (1980).

Murase, N., et al., Transplantation 55:701 (1993).

Noelle, R. J., et al., FASEB 5(13):2770 (1991).

O'Gara, A. and Defrance, T.: "Bioassays for interleukins", *In Laboratory Methods in Immunology*, H. Zola, Ed. CRC Press (1990).

Ono and Lindsey, J. Thor. Cardiovasc. Surg. 57(2):225–29 (1969).

Platt, J. L., et al., Immunol. Today 11(2):450 (1990).

Pu, L., et al., *Zhongguo Yaoli Xuebao* 11:76 (1990).

Roberts, J. P., et al., Ann. Rev. Med., 40:287 (1989).

Roitt, L., *Essential Immunology*, 7th edition, Blackwell Sci Pub, p. 63 (1991).

Storb, R., "Pathophysiology and Prevention of Graft-Versus-Host Disease," in *Advances in Immunobiology: Blood Cell Antigens and Bone Marrow Transplantation*, McCullogh, J., and Sandler, S. G., editors, Alan R. Liss, Inc., New York, p. 337 (1984).

Storb, R., Blood 66:698 (1985).

Storb, R., et al., N. Engl. J. Med. 314:729 (1986).

Viswanathan, N. I., et al., *J. Chem. Soc. Perk. Trans. I*, 2:349 (1979).

Wang, J., and Morris, R. E., Transplantation Proc. 23:699 (1991).

Watson, J., et al., J. Exp. Med. 150:849 (1979).

Wu, Q., et al., *Jiegou Huaxue* 11:55 (1992).

Zhang, W., et al., *Acta Pharm. Sin.* 21:592 (1986a).

Zhang, L., et al., *Zhongguo Yaoli Xuebao* 7:85 (1986b).

Zhang, W., et al., *Shanghai Yike Daxue Xuebao* 13:267 (1986c).

Zhang, D. M., et al, *Yaoxue Xuebao* 27:638 (1992).

BACKGROUND OF THE INVENTION

A variety of immunosuppressive agents have been used in treating or preventing transplantation rejection. Organ transplantation involving human organ donors and human recipients (allogeneic grafts or allografts), and non-human, e.g. primate or porcine, donors and human recipients (xenogeneic grafts or xenografts), has received considerable medical and scientific attention (Roberts, 1989; Platt, 1990; Keown, 1991; Wang, 1991; Hasan, 1992; Murase, 1993). To a great extent, this effort has been aimed at eliminating, or at least reducing, the problem of rejection of the transplanted organ. In the absence of adequate immunosuppressive therapy, the transplanted organ is destroyed by the host immune system.

From follow-up studies on human transplant patients, as well as transplantation studies in animal model systems, the following features of transplant rejection have been established. The major targets in transplant rejection are non-self allelic forms of class I and class II major histocompatibility complex (MHC) antigens. Rejection is mediated by both antibodies and cytotoxic T lymphocytes (CTLs), with the participation of CD4+ "helper" T cells (Noelle, 1991). In general, foreign class I MHC antigens stimulate CD8+ CTLs, and foreign class II MHC antigens stimulate CD4+ T cells (Roitt, 1991).

Presently, there are several compounds which have been used to suppress allograft rejection in humans, including corticosteroids, cytotoxic drugs that specifically inhibit T cell activation such as azathioprine, immunosuppressive drugs such as cyclosporin A, and specific antibodies. In general, these compounds are not effective, or are only poorly effective, in suppressing xenograft rejection.

Antibodies and complement have been shown to be of primary importance in the rejection of xenografts (Hasan). This has led to proposed therapies designed to severely inhibit antibody production as a means of suppressing xenograft rejection (Hasan). However, such drastic treatment can lead to increased risk of death by infection.

Accordingly, it would be desirable to treat xenograft rejection with an immunosuppressant compound that is effective in such treatment, but at a dose level which substantially reduces side effects and permits effective treatment over a longer period.

SUMMARY OF THE INVENTION

The method of the invention is for suppressing xenograft rejection in a host subject. The method includes administering to the subject, an immunosuppressant drug, including cyclosporin A, FK506, azathioprine, rapamycin, mycophenolic acid, a glucocorticoid, or a cyclophosphamide, where the drug or amount of drug administered is, by itself, ineffective to suppress xenograft rejection in the subject. A potentiator, which is either (i) an ethanolic extract of *Triterygium wilfordii* or a (ii) purified triptolide component of the extract is administered in an amount effective to suppress xenograft rejection in the host in combination with the immunosuppressant drug.

An exemplary immunosuppressant drug is cyclosporin A, for use in combination with the *T. wilfordii* extract or a triptolide component thereof, as represented by 16-hydroxytriptolide, triptolide, and tripchlorolide.

The immunosuppressive drug and potentiator may both be administered at regular intervals over a time period of at least 2 weeks, and may be administered either orally or parenterally. The amount of immunosuppressant drug administered is typically between about 20% and 100% of the amount of drug needed to suppress xenograft rejection in the host.

These and other objects and features of the invention will become more fully apparent when the following detailed description of the invention is read in conjunction with the accompanying drawings.

BRIEF DESCRIPTION OF THE DRAWINGS

Fig. 5A is a plot of heart allograft transplant survival time for untreated animals (squares), and animals treated with purified TW extract by oral administration (circles) or intraperitoneal administration (triangles);

DETAILED DESCRIPTION OF THE INVENTION

I. Definitions

The terms below have the following meanings, unless specified otherwise:

"Immunosuppression therapy" refers to treatment of a mammalian subject, including a human subject, to suppress an autoimmune or immune response against a transplanted allogeneic or xenogeneic cell, tissue or organ, or to suppress graft-versus-host disease.

An "ethanol extract of the root xylem from *T. wilfordii*" refers to a composition containing ethanol-soluble components extracted from the root xylem of *T. wilfordii*; such a composition may include water-soluble components that are also soluble in ethanol. The extract may be relatively unpurified, or may exist in progressively more purified forms, as described below. For example, water-soluble components and components which bind to silica gel in the presence of chloroform-containing solvents may be removed from the extract.

"Potentiated immunosuppression activity" refers to enhanced efficacy in immunosuppression therapy, as demonstrated by an enhanced therapeutic effect at a given immunosuppressant drug dose, or by equivalent therapeutic effect at a reduced immunosuppressant drug dose.

Xenograft rejection is "effectively suppressed" or "suppressed" in a host if the survival time of the xenograft in the host is extended by a statistically meaningful period over the survival time in the host in the absence of graft-suppression therapy. Typically, an effective suppression of xenograft rejection is a period of at least or more weeks, and may be up to several months or more.

Figure 3A:
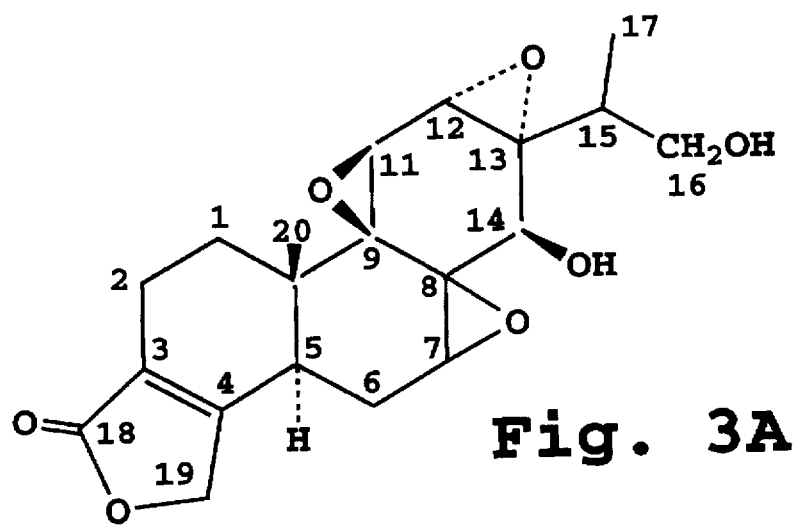
FIGS. 3A–3H show chemical structures of several purified TW compounds for use in the invention.
Figure 3B:
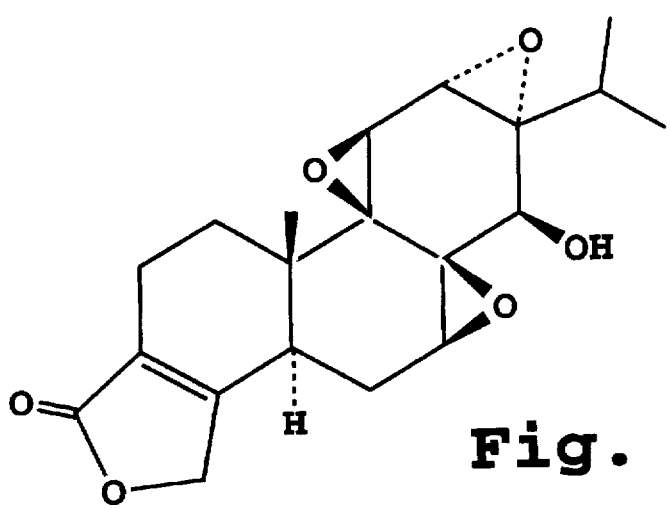
Figure 3C:
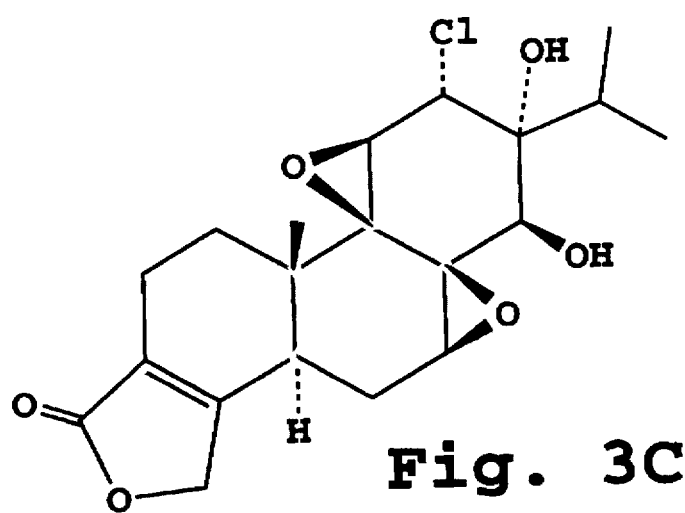
Figure 3D:
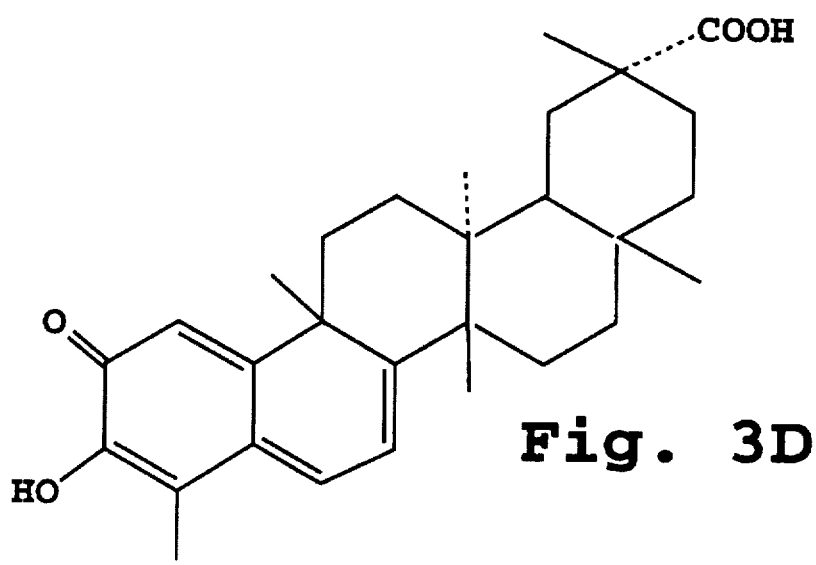
Figure 3E:
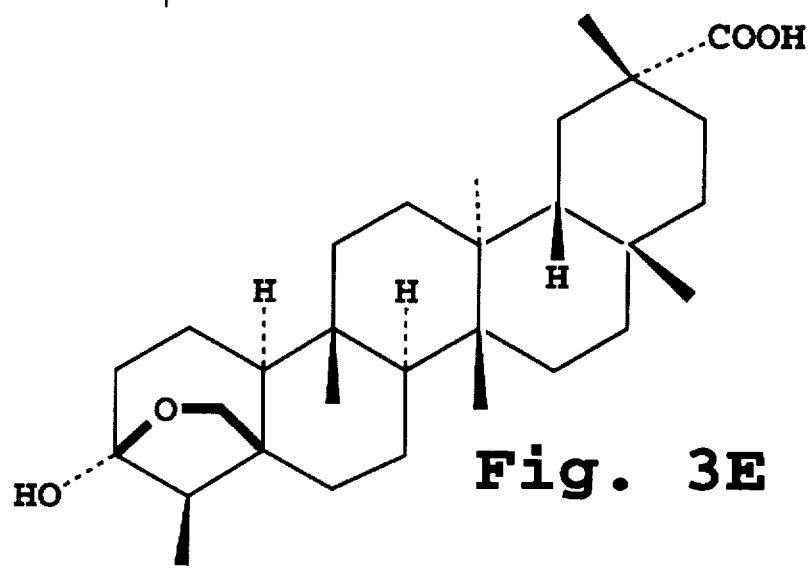
Figure 3F:
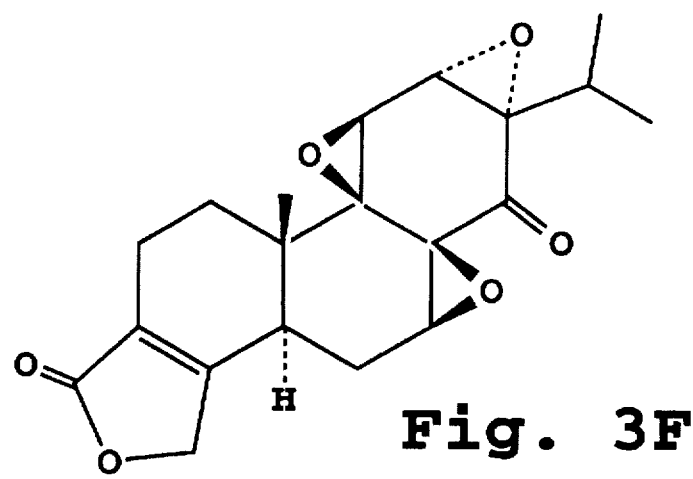
Figure 3G:
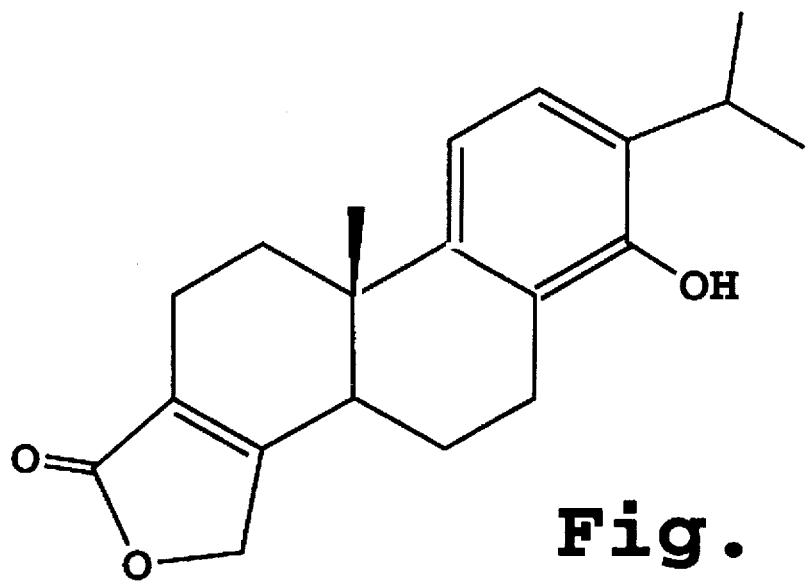
Figure 3H:
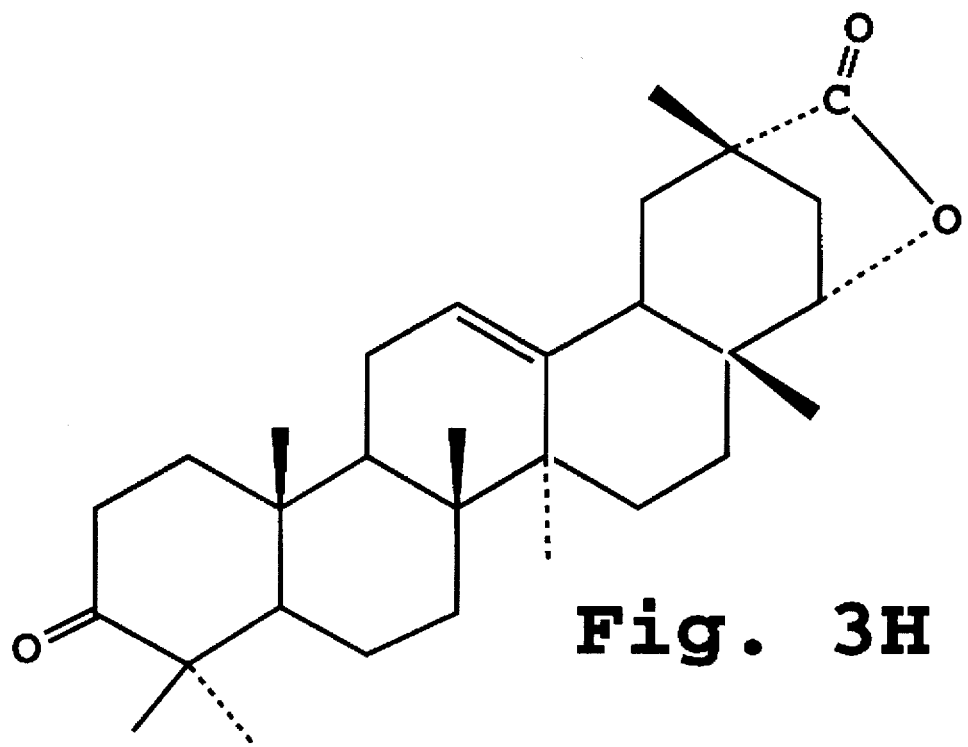

By "triptolide compound" or "triptolide component" is meant a compound having the parent structure of compound 3 B (triptolide) and analogs having one or more substituent modifications to the parent structure, such as the 16-hydroxyl group modification in FIG. 3A, the halo addition modification in FIG. 3C, the ring keto group modification in FIG. 3F, and epoxide group modifications in FIG. 3G.

I. TW Extract and Purified TW Compounds

A. Preparation Methods

Figure 1:
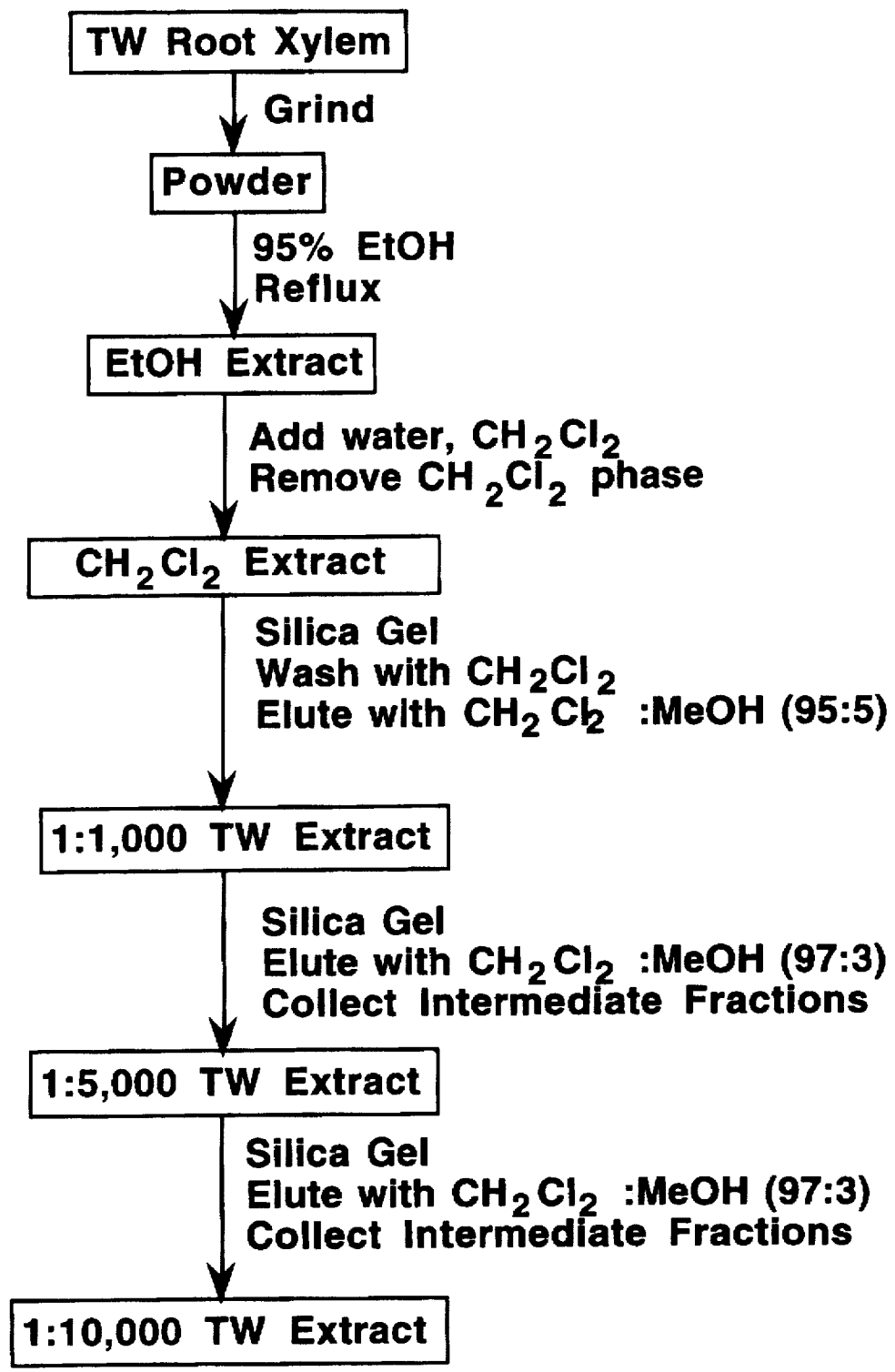
FIG. 1 is a flow diagram of a method for preparing a *Tripterygium wilfordii* (TW) ethanol extract, in accordance with the invention, also showing additional purification methods that may be used to achieve more purified forms of the extract for use in the composition of the invention.

The TW extract of the invention is obtained from the root xylem of *Tripterygium wilfordii* (TW), a medicinal plant which is grown in the Fujiang province and other southern provinces of China. Plant material can be obtained in China or through commercial sources in the United States. One method of preparation of a TW ethanol extract is illustrated in FIG. 1, and detailed in Example 1. Briefly, dried plant material is ground into a crude powder and then extracted by boiling in 95% ethanol with refluxing. The ethanol is removed and the extraction typically repeated twice. The resulting extracts are then combined and the ethanol removed (for example, by evaporation or heat-assisted evaporation). About 10 g dry ethanol extract is usually recovered per kg dry weight of plant material. This simple ethanol extract represents one preparation useful in the practice of the treatment method of the present invention. The extract is composed of plant components which are extractable from *T. wilfordii* root xylem by ethanol.

The ethanol extract from above may be further purified, to remove components, for example, which do not contribute to the potentiation of other immunosuppressant drugs. An exemplary purification method is shown in FIG. 1, and detailed in Example 2. Briefly, the ethanol extract from above is filtered and the volume is reduced under vacuum. The resulting syrup is diluted with water. Chloroform-soluble components are extracted by adding chloroform, separating the non-aqueous-phase material, and discarding the aqueous-phase components. The chloroform extract can be concentrated, e.g., by evaporation, and applied to a silica gel column. The extract material is then eluted successively with chloroform and chloroform:methanol (95:5) at a yield of about 1 g extract material per 20 g of original ethanol extract, corresponding to about 100 g dry weight starting plant material.

This partially purified extract is referred to as a 1:1000 TW extract. The extract includes ethanol extract components limited to those components which are further extractable from ethanol:water (2:1) by methylene chloride, and are further retained on silica gel in 100% methylene chloride.

The 1:1000 extract can be further purified (Example 2) by application to a silica gel column and elution with methylene chloride:methanol (97:3). Typically, six fractions are collected with the first and last of the six fractions being discarded. The four intermediate eluted fractions are combined, with a yield of about 20 g material per 100 gram 1:1000 extract. The resulting extract is referred to herein as a 1:5000 extract, and contains plant components further limited to those methylene components which are elutable from silica gel by chloride:methanol (95:5), and are further elutable from silica gel using methylene chloride:methanol (97:3).

The 1:5000 extract can be further purified by the same procedure, i.e., by elution from silica gel with methylene chloride:methanol (97:3) and collection of the intermediate fractions, with a final yield of about 1 g material per 2 gram 1:5000 extract. This purified extract is referred to herein as a 1:10,000 extract, and includes components which are contained in the intermediate fractions which are eluted from a silica gel column by elution with methylene chloride:methanol (97:3).

It will be appreciated that the above purification steps are exemplary of the types of purification procedures that may be employed, if desired, to remove unneeded components from the ethanol-soluble TW extract. A variety of other chemical purification methods known to those skilled in the art may also be employed.

Figure 2A:
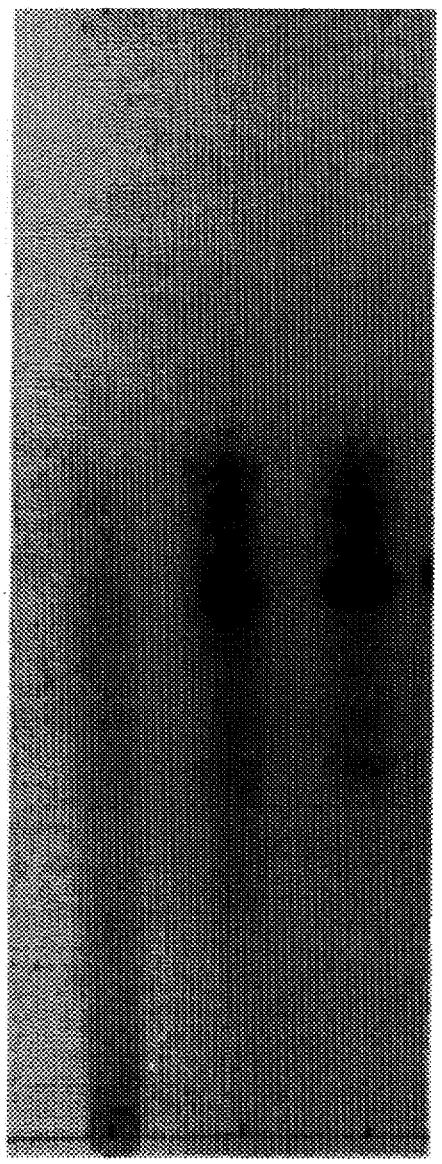
FIG. 2A is a thin layer chromatogram of 1:1,000 TW extract (Lane A), 1:5,000 extract (Lane B) and purified 1:10,000 TW extract (Lane C)

FIG. 2A shows a thin-layer chromatogram of the various TW extract preparations prepared as above. Thin-layer chromatography and the chemical assays were carried out as described in Example 3. These experiments showed that (1) purification between the 1:1,000, 1:5,000 and 1:10,000 extracts (lanes A, B, and C, respectively) has removed a number of major plant components; and (2) the 1:1000, 1:5000, and 1:10,000 extracts contain no alkaloids, as determined using the Dragendorff reagent.

Chemical structures of purified TW compounds for use in the invention are illustrated in FIGS. 3A–3H. The structure of 16-hydroxytriptolide is shown in FIG. 3A. A purification procedure for this compound is described, for example, in PCT publication No. WO 94/26265 published Nov. 24, 1994, which is incorporated herein by reference. FIG. 3B shows the structure of triptolide, which can be obtained in pure form by methods described in Kupchan et al. (1972), Kupchan et al. (1977), and Pu et al. (1990). Tripchlorolide, shown in FIG. 3C, can be prepared from TW by methods described in Zhang et al. (1992), Lu et al. (1990; 1991), and Zhang et al. (1986a), or can be prepared synthetically from triptolide as described in Ma et al. (1992). Celastrol (FIG. 3D) can be purified as described in Johnson et al. (1963) and Zhang et al. (1986a,b). Salaspermic acid (FIG. 3E) can be purified as described in Viswanathan et al. (1979), Zhang et al. (1986a), and Kashiwada et al (1992). Triptonide (FIG. 3F) can be purified as described in Kupchan et al. (1972), Wu et al. (1992), and Zhang et al. (1986c). Triptophenolide (FIG. 3G) can be purified as described in Deng et al. (1982; 1992). Wilforlide B can be purified by the method of Quin et al. (1982). Tripdiolide (structure not shown) can be purified as described in Kupchan et al. (1972; 1977).

B. Biological Properties of Purified Extract

The 1:10,000 extract from above was examined for immunosuppressive activity in a variety of biological assays. The following properties were observed:

1. The extract inhibited peripheral blood lymphocyte (PBL) proliferation that was stimulated by anti-CD3 antibody (Example 4). Increasing amounts of purified TW extract produced dose-dependent inhibition of proliferation in both stimulated and unstimulated cells, in the concentration range from about 0.3–1.25 µg extract components/ml culture medium. At a concentration of 1.25 µg/ml, the extract inhibited proliferation of unstimulated PBLs 36-fold, and inhibited proliferation of stimulated PBLs 860-fold.

2. The effect of the purified TW extract on the production of the cytokines IL-1, TNF-$\alpha$, IL-2, and IL-6 was assessed by measuring the concentration of these cytokines in the culture medium of anti-CD3 stimulated and unstimulated human PBLs. Cytokine levels were measured by standard ELISA methods using commercially available kits. Briefly, assay buffer was added to each of the wells of a microtiter plate containing pre-bound anti-cytokine anti-body, followed by addition of standard or sample solution, diluted appropriately for the concentration range measured, followed by a second reporter-labeled antibody specific against the anti-cytokine antibody. Details are given in Example 5.

Figure 4:
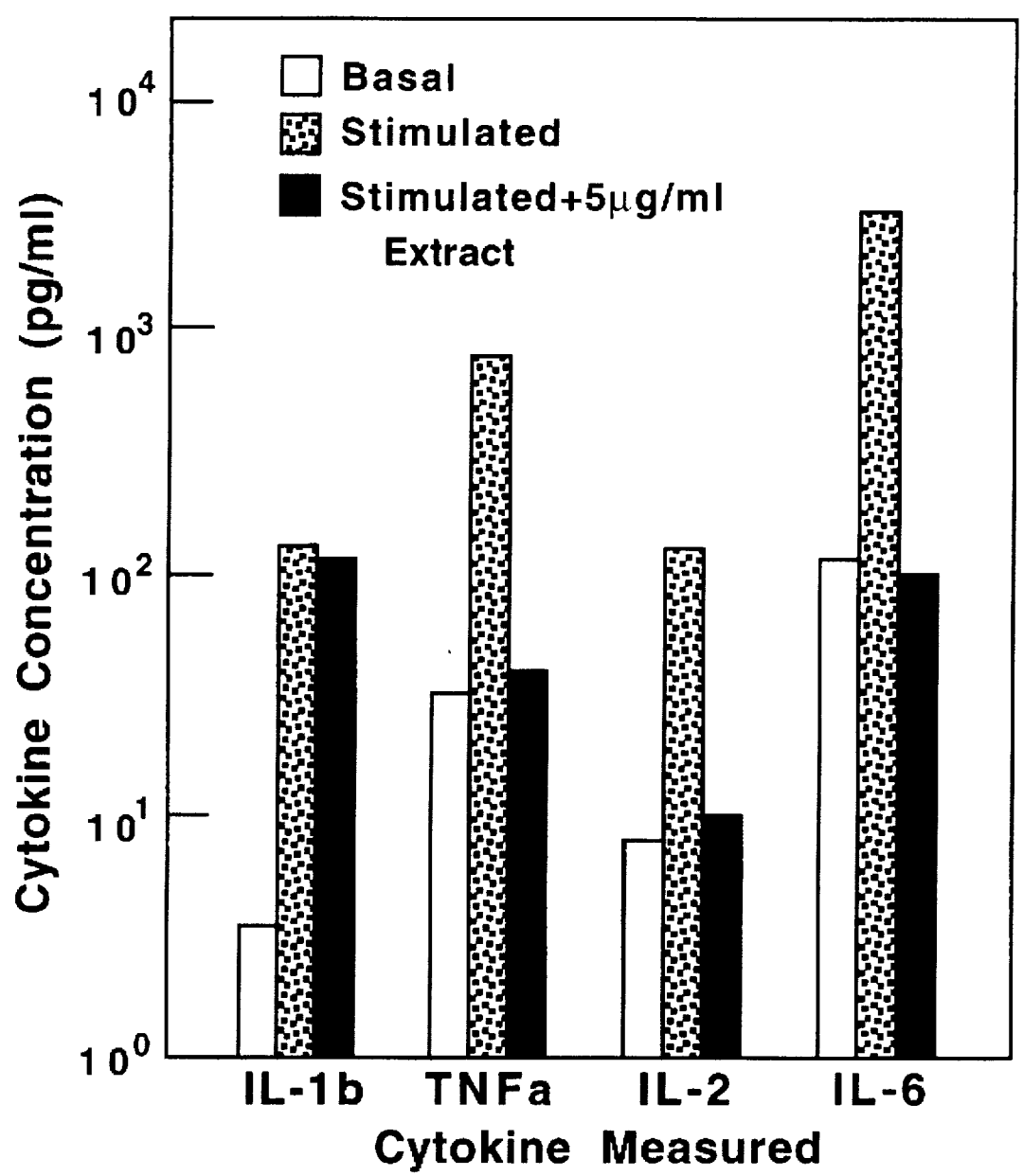
FIG. 4 shows the suppressive effect of a purified TW extract on production of IL-1β, TNF-α, IL-2, and IL-6 by human peripheral blood lymphocytes in culture.

FIG. 4 shows the levels of IL-1$\beta$, TNF-$\alpha$, IL-2, and IL-6 in human PBLs at basal levels (open bars), in cells stimulated with anti-CD3 antibody (shaded bars), and in anti-CD3 antibody-stimulated cells treated with purified TW extract (solid bars). Anti-CD3 stimulation resulted in a significant increase in all four cytokines measured. The purified TW extract significantly inhibited the production of TNF-$\alpha$, IL-2, and IL-6, whereas the extract decreased production of IL-1$\beta$ only slightly. Extract was added to the culture at a concentration of 5 µg/ml culture medium.

3. The ability of the extract to suppress the cell-proliferative effect of IL-1 in mouse thymocytes (O'Gara, 1990) was also examined. Almost complete inhibition of cell proliferation was observed in the range of 0.01 to 1 µg dried extract components/ml culture medium.

4. The extract also suppressed, but at higher concentration, the cell-proliferative activity of IL-2 on the IL-2 dependent cell line, HT-2, according to published methods (Watson, 1979).

5. Potential cytotoxicity of the extract was assessed by measuring the effect of the purified extract on the ability of cultured cells to reduce MTT (3-[4,5-Dimethylthiazol-2-yl] -2,5-diphenyltetrazolium bromide), an index of cellular respiration. This is a sensitive assay for the detection of cytotoxicity (Green, 1984). Details of the procedure are given in Example 6. In addition, staining with the vital dye trypan blue, which stains dead cells, was also carried out routinely in all of the culture systems described. Toxicity was evaluated in vitro in two different cell culture systems, human pBLs and mouse thymocytes. No cytotoxicity was observed at an extract concentration of 10 mg/ml in PBLs and 3.1 mg/ml in mouse thymocytes, the highest concentrations tested in each system.

6. A measure of in vivo immunosuppression is inhibition of cell proliferation in the mixed lymphocyte reaction (MLR) (Bradley; Mishell, 1980). In these experiments, mice were treated with the TW extract for 14 days. Spleen cells, the "responder" cells, were prepared and co-cultured with irradiated spleen cells prepared from a different mouse strain, the "stimulator" cells. The responder cells proliferate in the presence of the allogenic stimulator cells. Irradiation of the stimulator cells renders them unable to proliferate. After a 72-hour incubation, tritiated thymidine was added to the mixed cell cultures, and incorporation of the labeled nucleotide into DNA was measured as an index of cell proliferation.

In one study, C3H mice were injected intraperitoneally with either 1 or 10 mg purified TW extract/kg body weight. Animals were treated daily for 14 days prior to harvesting the spleen cells. Spleen cells from C3H mice were cultured with irradiated spleen cells from BalbC or C57 Black (C57Bl) mice. Irradiated spleen cells from C3H mice served as controls.

Irradiated allogeneic spleen cells were found to stimulate C3H cell proliferation two- to four-fold, in comparison with irradiated syngeneic cells. The extract effectively inhibited the mixed lymphocyte response, and was dose dependent in the range 1–10 mg/kg animal weight.

In a similar series of experiments, C3H mice were treated for 14 days with 10 mg purified TW extract/kg body weight or with diluent alone. Spleen cells were harvested and their response to the mitogens phytohemagglutinin (PHA) and concanavalin A (ConA) was assessed. A similar immunosuppressive effect by the extract was observed.

III. Formulations

In the immunosuppressant therapy method of the invention, the TW extract or one or more purified TW compounds may be administered with an immunosuppressant drug together in the same formulation, or separately in separate formulations. Where separate formulations are used, the TW extract or compound and the immunosuppressant drug can be administered by different routes.

The immunosuppressant drug which is administered with the TW compound is preferably one of the following:

(a) Cyclosporin A or cyclosporin C ("cyclosporin"), a non-polar cyclic oligopeptide;

(b) FK506, a fungal macrolide immunosuppressant;

(c) azathioprine, or 6-[(1-methyl-4-nitro-1H-immidazole-5yl)thio]1H-purine;

(d) methotrexate, (e) rapamycin, a fungal macrolide immunosuppressant;

(f) mycophenolic acid, or 6-(1,3-Dihydro-4-hydroxy-6-methoxy-7-methyl-3-oxy-5-isobenzofuranyl)-4-methyl-4- hexanoic acid; and (g) an immunosuppressant glucocorticoid, such as prednisone or dexamethasone.

The proportions of the two components (TW extract/compound and immunosuppressant drug) are preferably in the range of 1:50 to 50:1 by weight.

The TW extract/compound(s) and immunosuppressive drug may be administered to a subject orally, transdermally or parenterally, e.g., by intravenous, subcutaneous, intraperitoneal, or intramuscular injection.

When the TW extract/compound and immunosuppressant drug are employed in the form of solid preparations for oral administration, the preparations may be tablets, granules, powders, capsules or the like. In a tablet formulation, the compound is typically formulated with additives, for example, an excipient such as a saccharide or cellulose preparation, a binder such as starch paste or methyl cellulose, a filler, a disintegrator and so on, all being ones usually used in the manufacture of medical preparations.

For use in oral liquid preparation, the compounds/drugs may be prepared as a liquid suspension, emulsion, or syrup, being supplied either in liquid form or a dried form suitable for hydration in water or normal saline.

The compounds/drugs may be injected in the form of aqueous solutions, suspensions or oil or aqueous emulsions, such as liposome suspensions. Typically, for parenteral administration, the compounds/drugs are formulated as a lipid formulation, e.g., triglyceride, or phospholipid suspension.

IV. Treatment Method

The TW compounds and immunosuppressant drugs of the invention are employed in immunosuppression therapy, particularly in treating transplantation rejection or autoimmune disease.

According to an important feature of the invention, the effective dose of immunosuppressant drug is reduced significantly by coadministration (either concomitantly or separately) of the drug with the purified TW compound, allowing higher drug doses to be administered and/or more prolonged treatment while reducing deleterious side effects.

Table 3 below gives a list of autoimmune diseases which are appropriate for immunotherapy.

TABLE 3

| Autoimmune Diseases | |
| --- | --- |
| Disease | Tissue Affected |
| Addison's disease | adrenal |
| Allergies | inflammatory cells |
| Asthma | bronchi |
| Atherosclerosis | vessel walls |
| Crohn's disease | intestine |
| Diabetes (Type I) | pancreas |
| Graves' disease | thyroid |
| Guillain-Barré Syndrome | nerve cells |
| Lupus erythematosus | multiple tissues |
| Multiple sclerosis | nerve cells |
| Myasthenia Gravis | neuromuscular junction |
| Psoriasis | skin |
| Primary biliary cirrhosis | liver |
| Rheumatoid arthritis | joint lining |
| Uveitis | eye |

In treatment of an autoimmune condition, the patient is given the TW compound and immunosuppressive drug in a pharmaceutically acceptable vehicle or vehicles on a periodic basis, e.g., 1–2 times per week at a dosage level sufficient to reduce symptoms and improve patient comfort. Where the TW compound and immunosuppressant drug are administered separately, they may be administered with different dosing schedules as appropriate to maintain the potentiating effect of the TW compound on the immunosuppressant compound.

For oral administration, the TW compound may be given in liquid, tablet or capsule form, at a preferred dose of 0.1 and 10 mg/kg patient body weight per day. The dose may be increased or decreased appropriately depending on the response of the patient, and patient tolerance.

A parenteral suspension can be administered by injection, e.g., intravenously, intramuscularly, or subcutaneously, inhalation, or uptake via a mucosal membrane. Where the TW compound is TW ethanol extract, 16-hydroxytriptolide, triptolide, or tripchlorolide, a dose between about 0.05 and 1 mg/kg body weight per day is preferred, and this level may be increased or decreased appropriately, depending on the conditions of disease, the age of the patient, and the ability of the patient to resist infection. Where the TW compound is celastrol, salaspermic acid, triptonide, triptophenolide, wilforlide B, or tripdiolide, somewhat higher dosages may be necessary to achieve the immuno-potentiating effect on the immunosuppressant drug.

Where the TW compound is 16-hydroxytriptolide, triptolide, or tripchlorolide, the dosage of TW compound is preferably effective to achieve a serum concentration of between about $10^{-8}$ and $10^{-7}$M.

The dose of the immunosuppressant drug is preferably 25–75% of the dose that would be administered when given in the absence of the TW compound, although lower levels of immunosuppressant drug may be administered.

For treating rheumatoid arthritis, the TW extract/compound(s) and immunosuppressive drug may be administered by intravenous injection or by direct injection into the affected joint, for example. The patient may be treated at repeated intervals of at least 24 hours, over a several week period following the onset of symptoms of the disease in the patient.

For the treatment of systemic lupus erythematosus (SLE), as another example, TW extract/compounds(s) may be administered by oral or parenteral administration, such as intravenous (IV) administration.

For therapy in transplantation rejection, the method is intended particularly for the treatment of rejection of heart, kidney, liver, and bone marrow transplants. The method is useful in the treatment/inhibition of xenograft rejection as well as allograft rejection. The method may also be used in the treatment of graft-versus-host disease, in which transplanted immune cells attack the allogeneic host. The composition may be administered chronically to prevent graft rejection, or in treating acute episodes of late graft rejection.

Treatment is typically begun perioperatively and is typically continued on a daily dosing regimen, for a period of at least several weeks, for treatment of acute transplantation rejection. During the treatment period, the patient may be tested periodically for immunosuppression level. Biopsy of the transplanted tissue may also be appropriate.

In accordance with another embodiment of the invention, the immunosuppressant drug and TW extract/compound(s) are administered separately. The immuno-suppressant drug is administered in a therapeutically effective dose, typically between about 20–75% of the normal dose for the drug alone. Drug administration is typically by oral or parenteral routes. The TW extract/compound is then administered in an amount effective to potentiate the action of the immunosuppressant drug. Typically, the TW ethanol extract is administered orally, at a dose in the range 1–25 mg dried extract material/kg body weight.

A. Treatment/Inhibition of Allograft Transplant Rejection

The treatment of transplantation rejection, in accordance with the invention is illustrated for rejection of an allograft by the heart transplantation model used in Example 7. The method involves a well-characterized rat model system (Ono and Lindsey, 1969) in which a transplanted heart is attached to the abdominal great vessels of an allogeneic recipient animal, and the viability of the transplanted heart is gauged by the heart's ability to beat in the recipient animal.

FIG. 5A illustrates the effect of treatment with TW extract alone on allograft survival. As detailed in Example 7A, three animal groups were treated with either (a) 5% alcohol solution (squares), (b) 10 mg/kg purified TW extract (1:10,000) administered daily by oral administration (circles), or (c) 10 mg/kg purified TW extract administered daily by intraperitoneal injection (triangles). There were three animals in each group. Cardiac allograft survival was measured by the presence of detectable graft heart beat.

As seen from FIG. 5A, the heart grafts were rejected by the untreated recipient animals following an average of 6.7 days. In the animals treated with purified TW extract by oral administration, the allografts remained viable for 17 days, 3 days following discontinuation of treatment. In the animals treated with purified TW extract by intraperitoneal injection, the allografts remained viable for an average of 21.3 days, one week after discontinuation of treatment. There was no evidence of toxicity in the treated animals.

In a second study, transplant recipients were treated from one day preceding to 52 days following heart transplantation with (i) control solution (5% ethanol, 10 ml/kg), (ii) purified TW extract (1:10,000) (oral administration, 10 mg/kg), (iii) cyclosporin A (intraperitoneal (IP) administration, 0.75 mg/kg), or (iv) cyclosporin A (0.75 mg/kg) in purified extract (10 mg/kg), administered IP and PO, respectively.

Figure 5B:
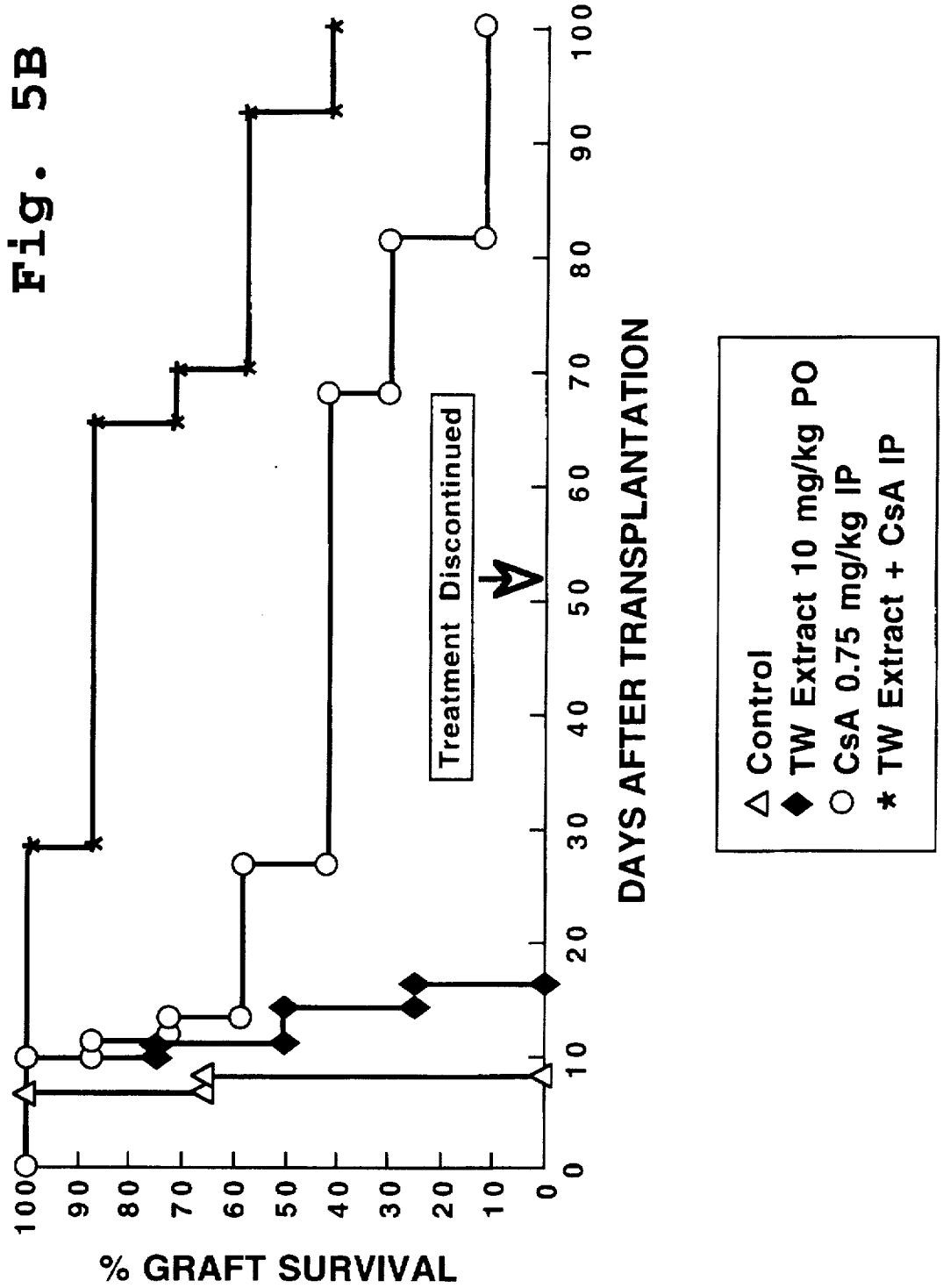
FIG. 5B is a plot of allograft transplant survival time for untreated animals (open triangles), and animals treated with TW extract alone (solid diamonds), cyclosporin A alone (CsA) (open circles), and CsA in a TW extract (* symbols)

As seen in FIG. 5B, the control group (no drug or extract) had a mean graft survival time of 6.7 days. In the group treated with the 10 mg/kg TW extract, mean graft survival increased to 11.8 days. With IP administration of cyclosporin A, mean graft survival time increased to 46.3 days, and there was a small percentage of grafts surviving at 100 days. The most effective results were observed in treatment with the composition in accordance with the invention, where mean graft survival time was 93.5 days, and half of the grafts survived to 100 days.

During the treatment period, only one graft was rejected in the group of recipient animals receiving both cyclosporin A and TW extract. In contrast, more than one-half of the grafts failed in the group treated receiving cyclosporin A alone.

According to an important feature, the invention provides a method for reducing the amount of immuno-suppressive drug required to effectively extend allograft compatibility, by coadministering to the subject a TW ethanol extract or purified TW compound. This is illustrated by the results shown in FIG. 6.

As detailed in Example 8, heart transplant recipient animals prepared were administered intraperitoneally (IP) various concentrations of cyclosporin A (CsA) alone or in combination with a range of TW extract concentrations (2.5, 5, and 10 mg/kg/day) for a 16 day period beginning one day prior to transplant. Survival percentages were recorded 21 days after transplant.

Figure 6:
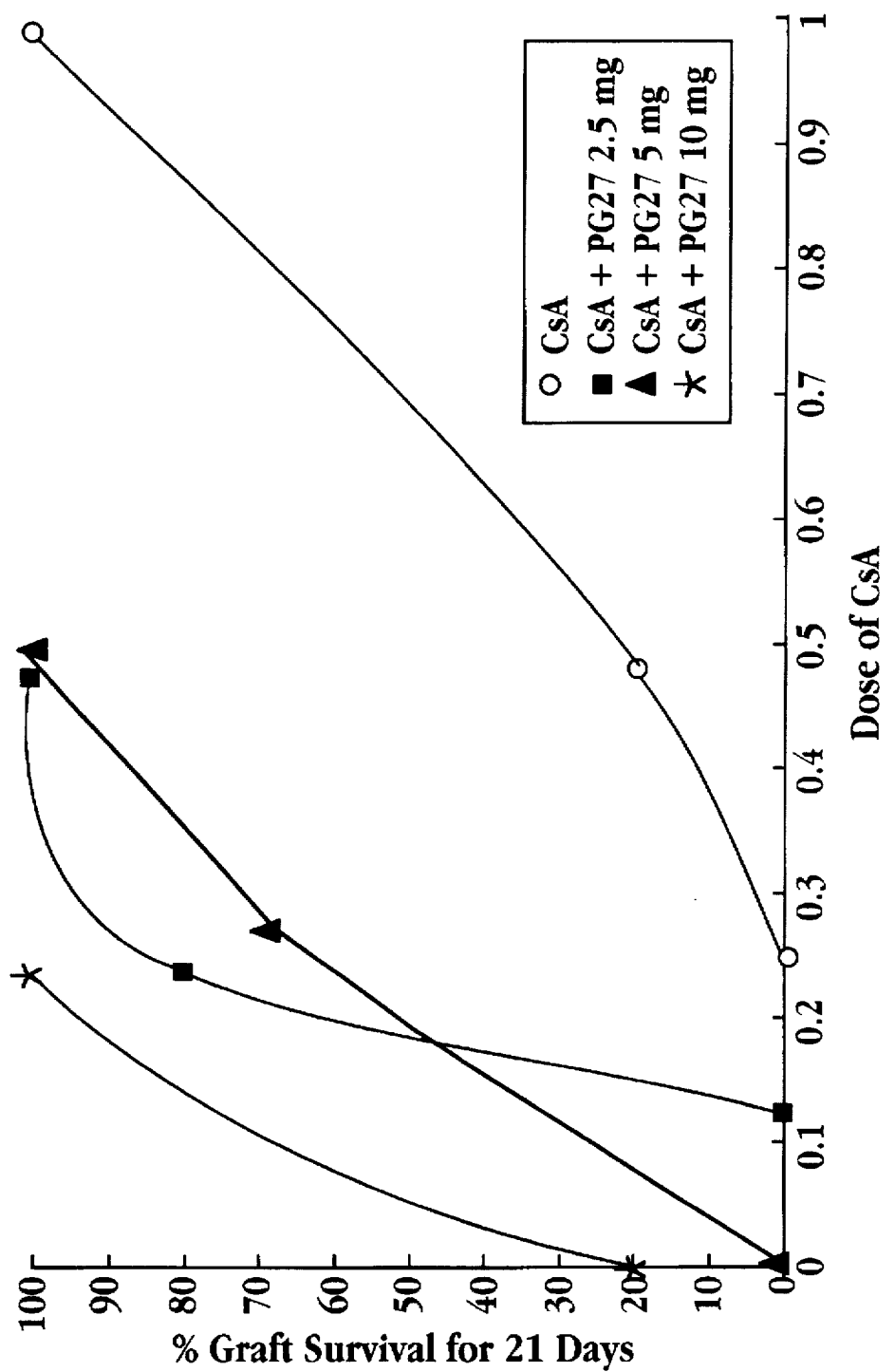
FIG. 6 is a plot of percent survival of allograft transplant recipients treated with CsA alone (open circles), CsA plus a TW extract (2.5 mg/kg/day, solid squares), CsA plus TW extract (5 mg/kg/day, solid triangles), and CsA plus TW extract (10 mg/kg/day, * symbols)

With reference to FIG. 6, treatment with CsA at a dosage of 1.0 mg/kg/day is 100% effective in preventing allograft rejection after 21 days, whereas dosages of 0.5 and 0.25 of cardiac allografts yield survival rates of about 20 and 0%, respectively. However, including TW extract at 2.5, 5, and 10 mg/kg/day substantially reduces the amount of CsA needed for 100% survival, from 1 mg/kg/day CsA in the absence of TW extract to about 0.25 mg/kg/day CsA in the presence of 10 mg/kg/day TW extract. It will be appreciated that by reducing the amount of CsA used, the method helps reduce or avoid the deleterious side-effects associated with CsA therapy.

Alternatively, the method of suppressing allografts may be practiced, in accordance with the invention, by combining subthreshold doses of an immunosuppression drug, such as cyclosporin A, with a purified triptolide compound, e.g., obtained synthetically or isolated from *T. wilfordii*. Preferred triptolide for use in the method are the ones illustrated in FIGS. 3A, 3B, 3C, 3F, and 3G, and particularly 3B and 3C. The dose of immunosuppressant drug used in the method is similar for that the *T. wilfordii* extract treatment, typically less than about ½–⅓ the dose normally required for immunosuppression when the drug is used alone. The dose of the purified triptolide employed in the method is typically 5–50% of the amount of total extract required for effective immunosuppression in the combination therapy.

B. Treatment/Inhibition of Xenograft Transplant Rejection

Figure 7A:
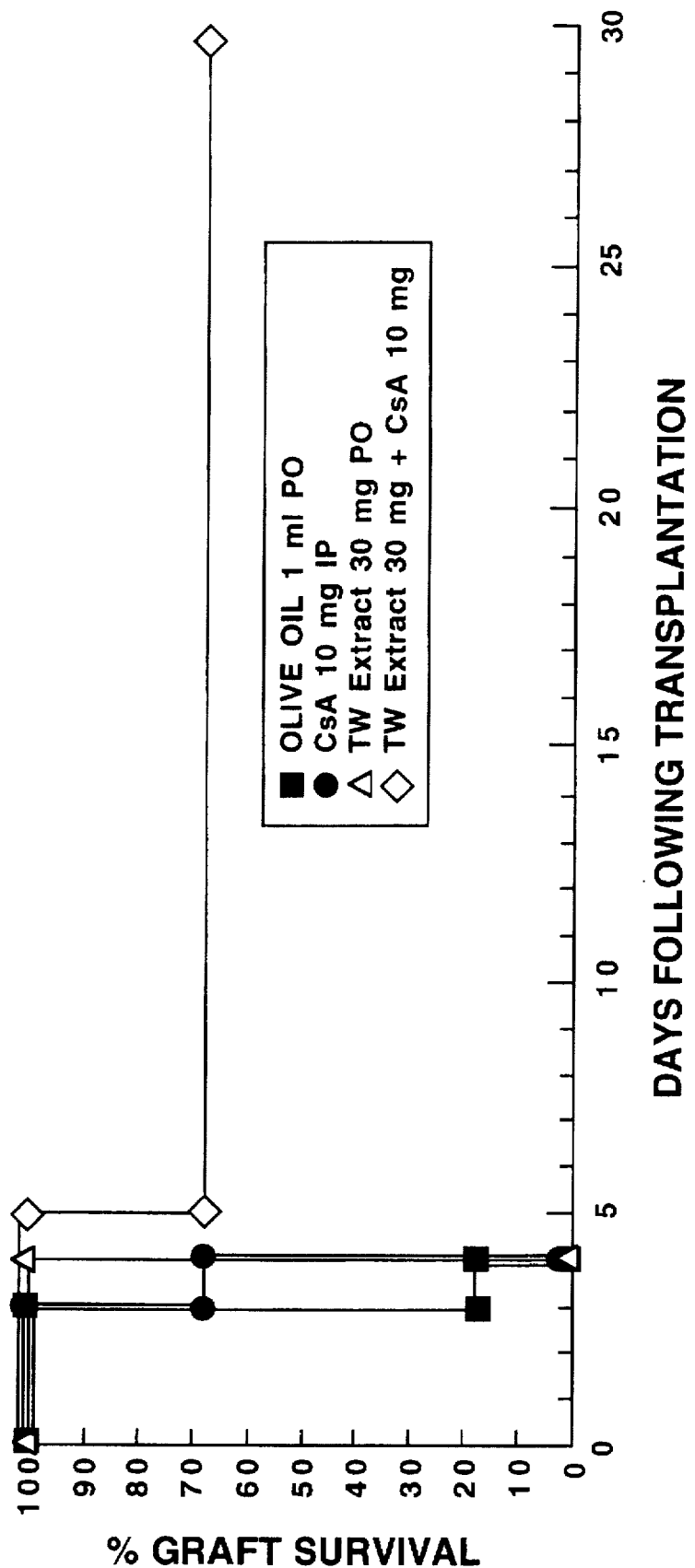
FIG. 7A is a plot of heart xenograft transplant survival time for untreated animals (solid squares), and animals treated with TW extract alone by oral administration (open diamonds), CsA alone by intraperitoneal administration (solid circles), and CsA (IP) plus a TW extract (oral) (open diamonds)

Inhibition of xenograft rejection was evaluated in a heart xenograft transplantation model (Example 9). These studies were carried out in the same manner as the allograft transplantation studies above, with the exception that the donor animals were hamsters (Wang, 1991; Murase, 1993). As seen in FIG. 7A, treatment with olive oil control solution resulted in a mean graft survival time of 3 days. Treatment with cyclosporin alone (10 mg/kg IP) or TW extract alone (1:10,000, 30 mg/kg PO) each resulted in a mean graft survival time of about 4 days. In contrast, treatment with cyclosporin A at 10 mg/kg, in combination with the TW extract at 30 mg/kg resulted in 2 of the grafts surviving longer than 30 days.

Figure 7B:
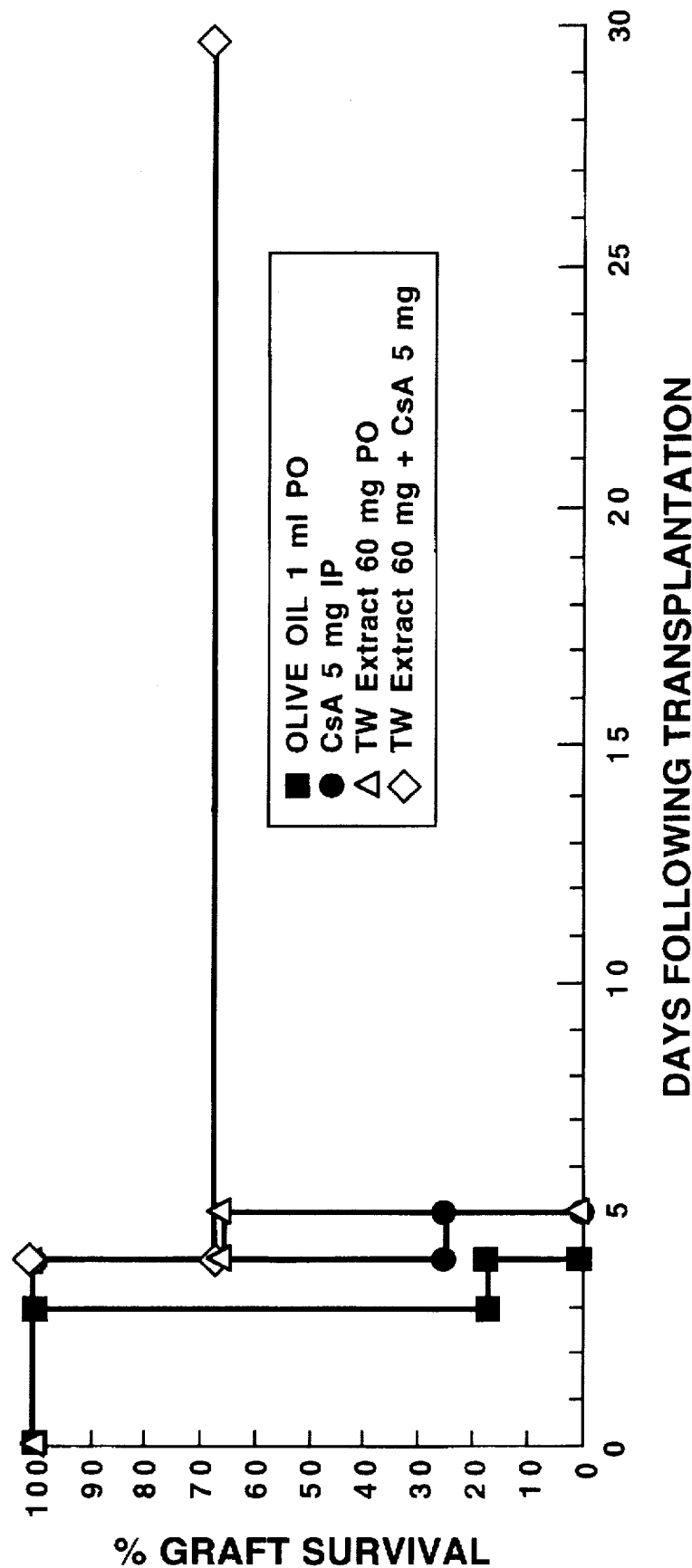
FIG. 7B is a plot of xenograft transplant survival time for animals treated as indicated in FIG. 7A, but with different CsA and TW extract amounts.

Using another regimen, in which the dose of cyclosporin A was reduced by half to 5 mg/kg, and the dose of TW extract doubled to 60 mg/kg, treatment with olive oil alone (control) resulted in a mean graft survival time of 3 days (FIG. 7B). Treatment with cyclosporin alone (5 mg/kg IP) resulted in a mean graft survival time of 4.3 days. Treatment with the TW extract alone (60 mg/kg PO) resulted in a mean graft survival time of 4.7 days. In contrast, treatment with cyclosporin A (5 mg/kg) in combination with TW extract (60 mg/kg) again resulted in 2 out of 3 grafts surviving longer than 30 days.

Figure 8:
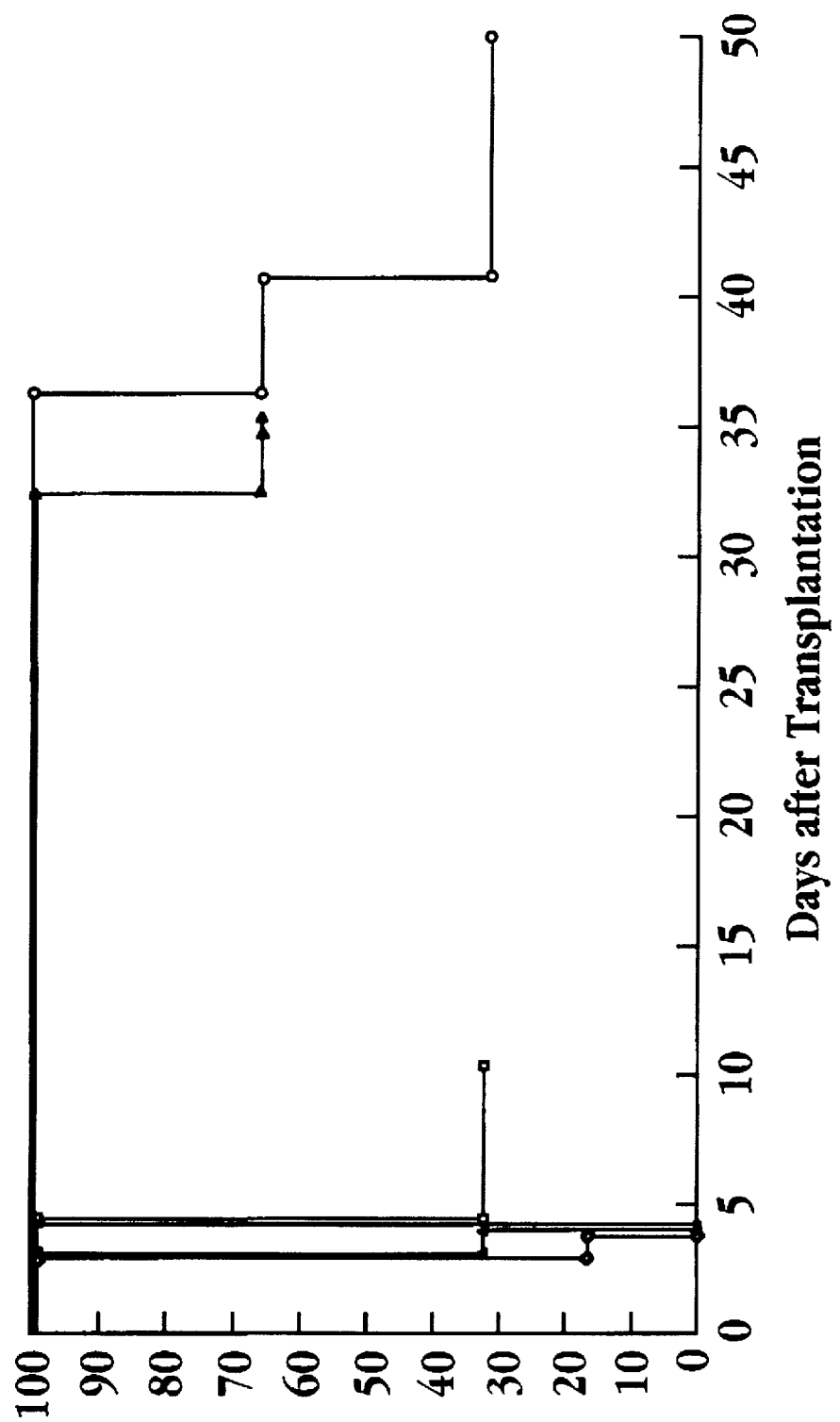
FIG. 8 is a plot of xenograft transplant survival time for recipient recipients treated with no drug (control, open diamonds), TW extract (solid circles), CsA alone (* symbols), azathioprine plus CsA (open squares), tripchlorolide plus CsA (open circles), and triptolide plus CsA (solid triangles)

Similarly improved results are obtained using CsA in combination with the purified TW compounds tripchlorolide and triptolide, as illustrated by the plot in FIG. 8 (Example 10). As can be seen, treatment with no drug, TW extract alone (30 mg/kg/day), or CsA alone (10 mg/kg/day) result in a survival time of about 4 days. Coadministration of CsA and azathioprine leads to a slight improvement, with 1 recipient surviving for 10 days. However, coadministration of CsA with either tripchlorolide or triptolide provided a significant improvement in survival time relative to administration of either alone, with all recipients surviving at least 31 and 34 days, respectively.

Example 11 describes a study showing that coadministration of the immunosuppressive drug, cyclosporin A, concurrently with TW extract or a purified TW compound leads to suppression of anti-xenograft antibodies. In one study, xenograft recipients were treated with no drug (control) TW extract (30 mg/kg/day), CsA alone (10 mg/kg/day), and TW extract (30 mg/kg/day) plus CsA at a lower dosage (5 mg/kg/day). Serum anti-xenograft antibodies (IgG and IgM) were measured until rejection, or until day 125 in the case of joint TW extract/CsA treatment. As can be seen from FIGS. 9A and 9B (IgG and IgM, respectively), untreated recipients quickly develop high anti-xenograft antibodies within the first 5 days following transplant, and these levels remained high for another 45 days. A similar increase is observed for treatment with TW extract alone, except that rejection was complete by about day 6. Antibody measurements with CsA alone are limited by rapid transplant rejection, which was complete by day 6. However, concurrent treatment with TW extract and CsA is effective to almost completely suppress anti-xenograft antibodies during administration for 100 days. When administration of the TW/CsA combination is stopped, anti-xenograft antibodies develop within a few days.

Figure 10A:
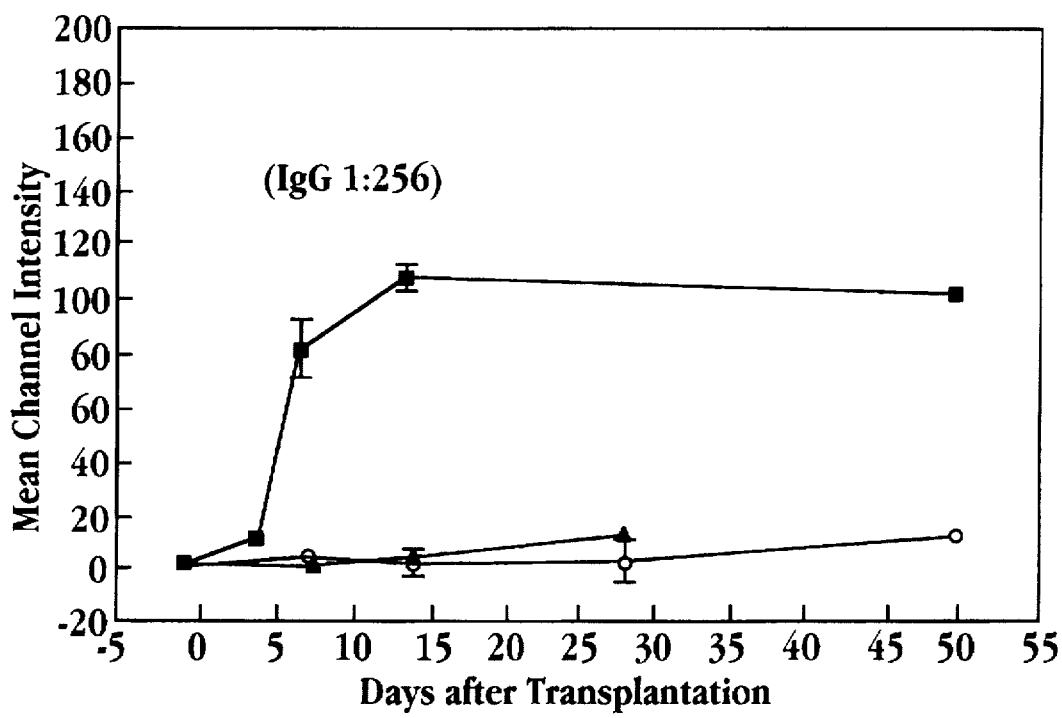
FIGS. 10A and 10B show plots of anti-xenograft IgG (10A) and IgM (10B) levels measured as a function of time in xenograft recipients treated with no drug (control, open squares), tripchlorolide plus CsA (open circles), and triptolide plus CsA (solid triangles)
Figure 10B:
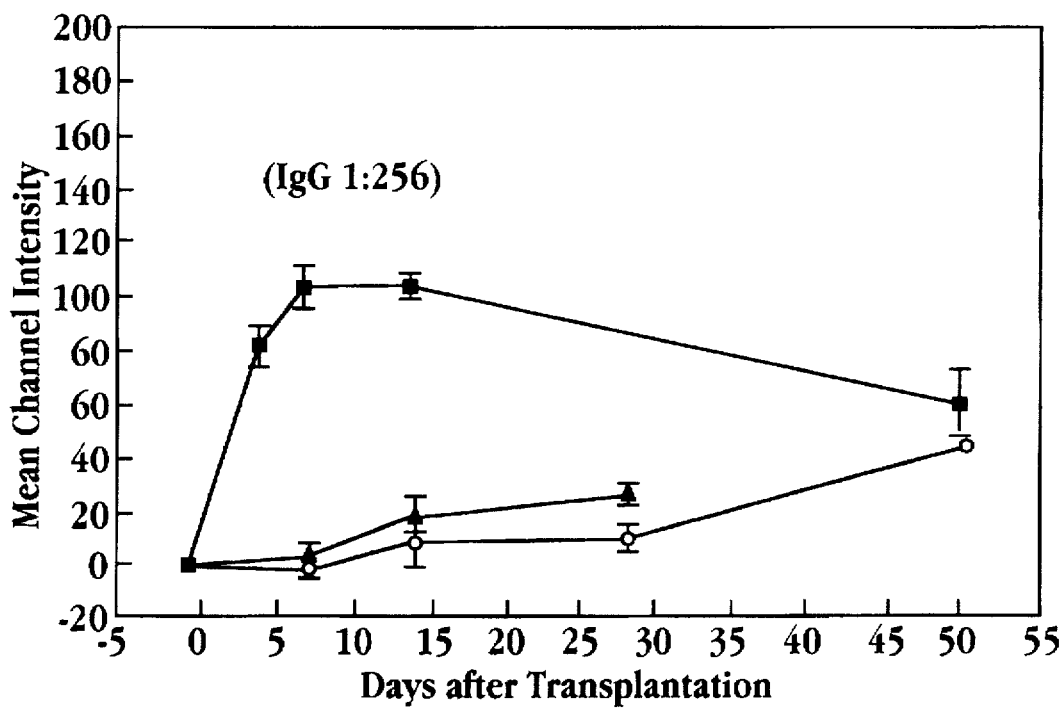

Similar trends are observed when CsA is administered in combination with tripchlorolide or triptolide, as illustrated in Figs. 10A and 10B. The joint administration is accompanied by substantial suppression of anti-xenograft antibodies for the duration of administration.

C. Treatment of Transplant Rejection with Extract Alone

In another aspect, the invention includes treating transplantation rejection by administering to a subject the TW extract alone. The extract is administered orally or parenterally, employing doses and dosing schedules such as given above. In one embodiment, the TW extract alone may be used to inhibit graft-versus-host disease (GVHD).

In one study, the TW extract was tested in a GVHD model that involves injection of normal $F_1$ mice with parental spleen cells. These mice develop a GVHD syndrome characterized by splenomegaly and immunosuppression (Korngold, 1978; Gleichmann, 1984).

In the study, detailed in Example 12, administration of TW extract was initiated one day before intravenous (IV) injection of allogeneic spleen cells, and treatment was continued daily through day 6 (one day before termination of the in vivo portion of the experiment on day 7). Dosing involved administering PO 0.1 ml/10 g of body weight of olive oil or olive oil containing the TW extract (30 mg extract/kg/day), or no administration at all. As a positive control, one group of mice received syngeneic $F_1$ rather than allogeneic C57Bl/6 splenocytes. As another control, measurements were carried out with untreated $F_1$ mice which did not receive cell transplants.

The $F_1$ host mice received $30 \times 10^6$ C57Bl/6 spleen cells IV on day 0 and were sacrificed on day 7. Single cell suspensions were prepared from individual spleens, and microwell cultures were established in the presence and absence of concanavalin A to assess the extent of mitogenic responsiveness. The results are shown in FIG. 11.

Figure 11:
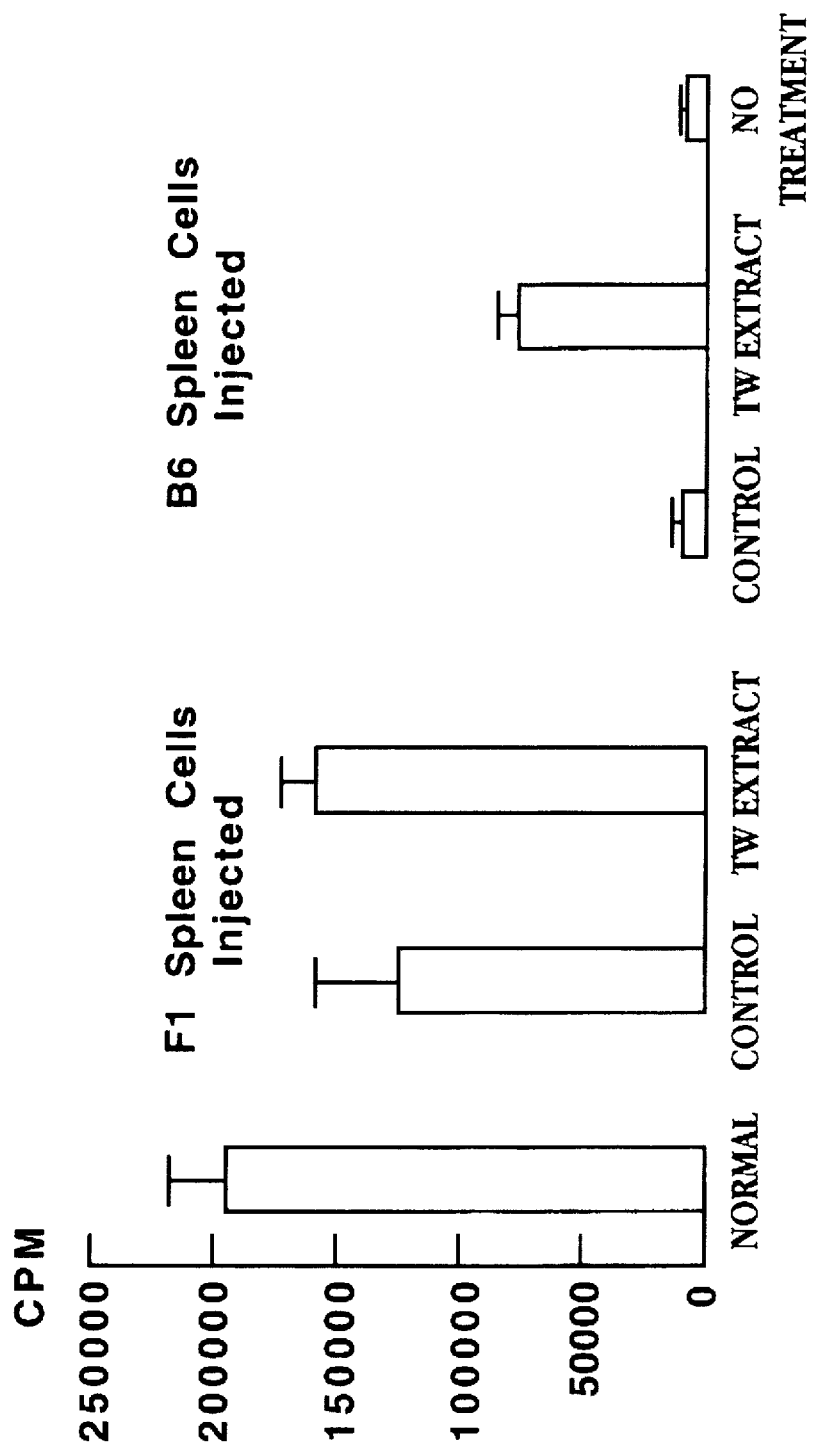
FIG. 11 is a bar graph showing the reversal, by a TW extract of the invention, of GVHD-induced suppression of the spleen cell response to concanavalin A, measured in a $^3$H-thymine incorporation assay.

As can be seen from the first three columns in FIG. 11 (left to right), $F_1$ mice that received $F_1$ cells and olive oil (control) showed a robust mitogenic response that was comparable to that seen in mice that had received neither drug injection nor cell transplant ("Normal"), as measured by the uptake of $^3$H-thymidine. Similarly, treatment of the $F_1$ cell recipient mice with TW extract (1:10,000) showed little effect (third column from left) relative to treatment with olive oil.

The recipients of allogeneic (B6) spleen cells and either no treatment or olive oil displayed a considerably reduced mitogenic response, consistent with the induction of GVHD (FIG. 11, columns 4 and 6). However, treatment of these mice with TW extract in olive oil showed an enhanced level of proliferation (column 5), indicating reversal of the suppressed response observed in the absence of TW extract. Moreover, the level of mitogenic reactivity achieved in this group approached that observed in the $F_1$ cell recipients that had been given olive oil (compare columns 5 and 2).

Figure 12:
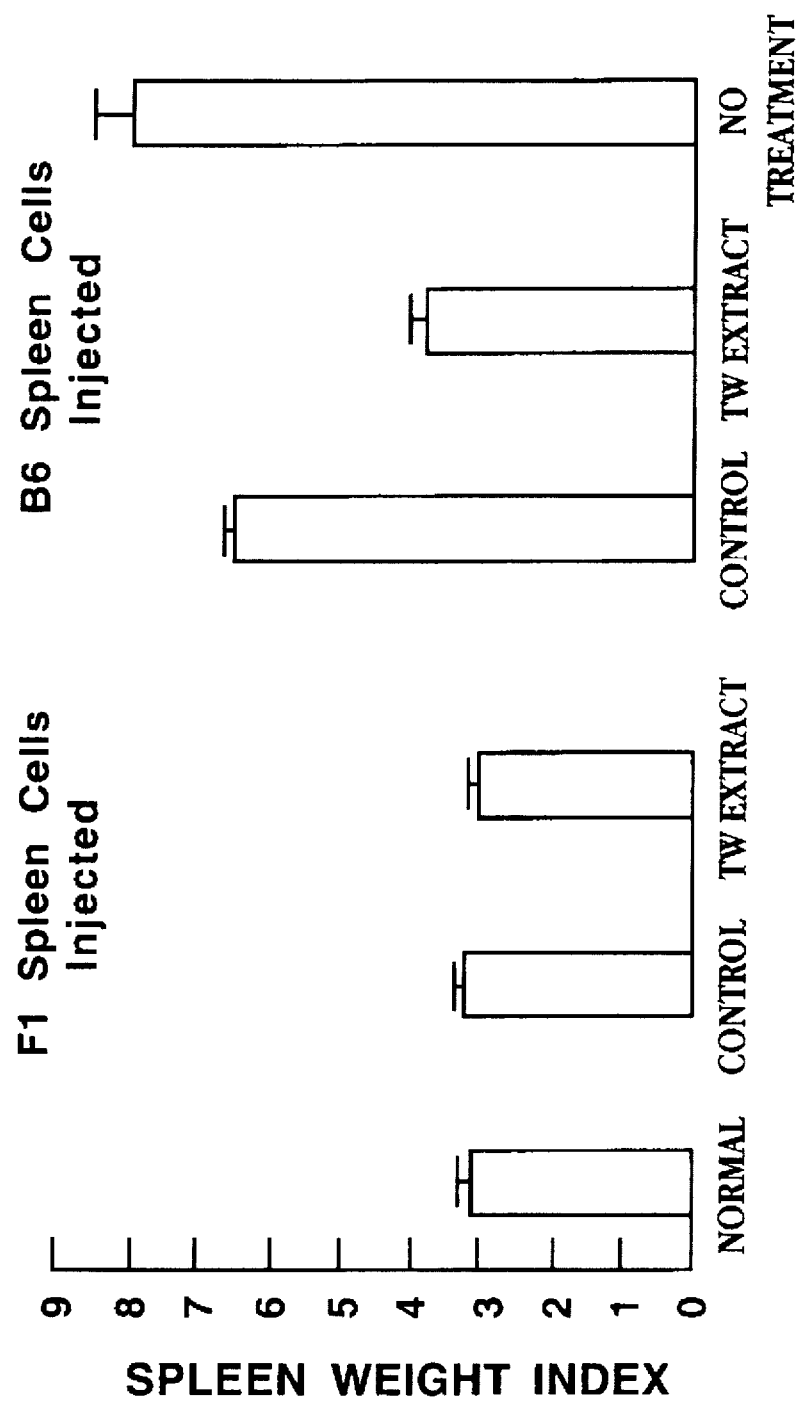
FIG. 12 is a bar graph showing a normalization, by a TW extract of the invention, of the spleen weight index in the model system used in FIG. 9.

In a related study, the TW extract was examined for its effect on the Spleen Index, which is the ratio of the spleen weight in mg to the body weight in grams. $F_1$ recipients receiving either B6 or $F_1$ spleen cells were administered PO olive oil or PO TW extract (1:10,000, 50 or 75 mg/kg/day) suspended in olive oil. Normal $F_1$ mice were included as a control, and $F_1$ recipients of $F_1$ spleen cells receiving olive oil or TW extract represent treated controls. The results are shown in FIG. 12.

As shown, the recipients of $F_1$ spleen cells showed no change in the Spleen Index (columns 1–3), compared with normal controls. This was expected since the transplanted cells were syngeneic. Mice receiving C57B1/6 cells and olive oil (column 4, "Control") displayed a markedly enhanced Spleen Index, consistent with induction of GVHD. In contrast, C57B1/6 spleen cell recipients treated with TW extract (1:10,000) afforded a Spleen Index that was not significantly different from that observed with the $F_1$ splenocyte-treated and normal control mice. Thus, the TW extract significantly reversed the GVHD condition caused by the transplanted C57B1/6 splenocytes.

In a third study (Example 13), TW extract was tested in a GVHD model that involves the transfer of bone marrow and spleen cells from an allogeneic mouse parental strain into lethally irradiated $F_1$ recipients (Fidler, 1993). The salient features of the model are that (i) untreated, irradiated mice die within about 2 weeks of irradiation, (ii) bone marrow and spleen cell transplantation prevent death from the irradiation, and (iii) in the absence of immunosuppressive drug therapy, transplant recipients die from GVHD after about 30 days.

Lethally irradiated recipient $BDF_1$ mice were injected with $30 \times 10^6$ spleen cells and $10 \times 10^6$ bone marrow cells from C57B1/6 donors. Administration of olive oil or TW extract (1:10,000, 30 mg/kg) suspended in olive oil was initiated one day before irradiation and continued daily for a total of 8 days. Mice were weighed and inspected daily for the first 3 weeks of the experiment and then at least 3 times per week for the next 8 weeks.

Figure 13:
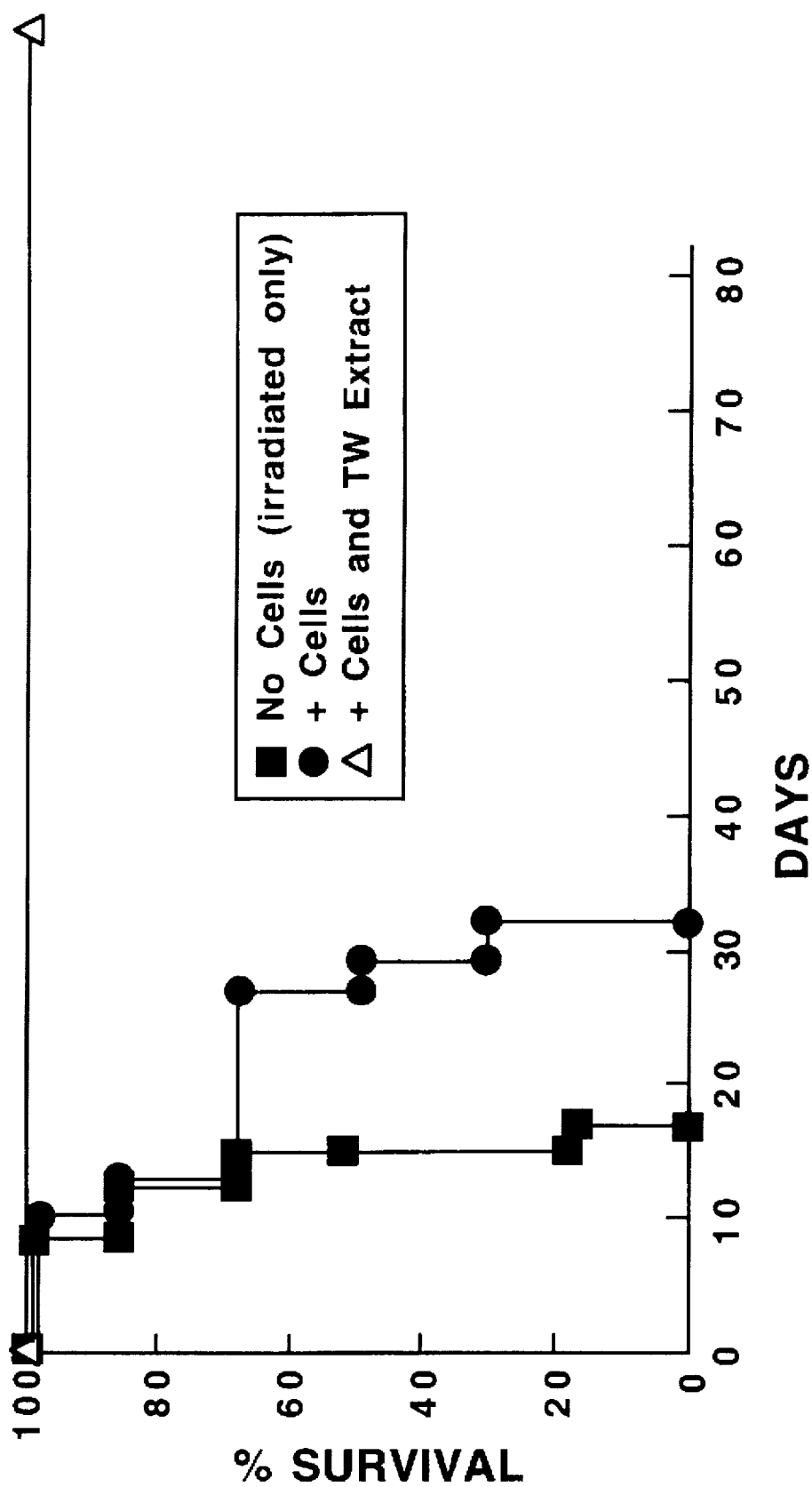
FIG. 13 is a survival plot of mice that were lethally irradiated and then treated with nothing (solid squares), allogeneic spleen and bone marrow cells (solid circles), or cells and TW extract.

As shown in FIG. 13, the control mice receiving no cell transfer died by day 16. Among the mice receiving allogeneic cells only, two died before day 10, a time frame that is characteristic of bone marrow failure after lethal irradiation. A similar event occurred with the TW extract-treated mice, where again, two mice died before day 10. It is likely that in these cases, the marrow transferred to these mice failed to engraft. The remaining mice receiving allogeneic cells only died by day 32, a time course consistent with death due to GVHD. However, no deaths were observed in the remaining TW extract-treated animals through day 135, and there were no signs of GVHD apparent in the survivors, such as ruffled fur or abnormal posture.

Irradiated control animals receiving no cells lost weight gradually after irradiation with some variation caused by the deaths of individual animals. Mice that had received allogeneic cells and then were treated with olive oil displayed weight loss over an extended time period. Ruffled fur and hunched postures, along with weight loss, are characteristic signs of GVHD. The mice treated with TW extract, on the other hand, appeared to recover from irradiation more quickly as evidenced by weight gain. Over the longer term, the weights of these mice remained stable.

By way of contrast, treatment of irradiated, allogeneic cell recipients with cyclosporin A, instead of TW extract, at concentrations of up to 10 mg/kg/day, failed to increase survival rate.

The results discussed above and illustrated in FIGS. 11–13 demonstrate that the TW extract of the invention is useful in treating graft-versus-host disease and transplantation rejection.

The following examples are intended to illustrate, but in no way limit the scope of the invention.

EXAMPLE 1

Preparing *Tripterygium wilfordii* Ethanol Extract

*Tripterygium wilfordii* plants were obtained in Fujiang province, China. Plants were air dried in sunlight. The root xylem of the plants (300 g) was ground into a crude powder and extracted with 5 volumes (1.5 l) of 95% ethanol, under reflux at 85° C. for 4 hours. The filtered xylem powder was then extracted two more times with 95% ethanol (900 ml each time). The three extracts (total of about 3.3 l) were combined and the resulting mixture was concentrated at 50° C. under vacuum, to about 2% of the original volume, i.e., about 66 ml.

EXAMPLE 2

Further Purifications of the TW Extract

A. The $CH_2Cl_2$ TW Extract

The ethanol extract syrup obtained in Example 1 was then diluted with 33 ml water, filtered through Whatman #1 filter paper. The filtrate was extracted 4 times (50 ml/extraction) with methylene chloride ($CH_2Cl_2$).

B. The 1:1000 TW Extract

The combined, $CH_2Cl_2$-extract filtrate (about 200 ml) was concentrated, and applied to a 1 cm (diameter)×5 cm column containing silica gel (1.5 kg; 60–200 mesh). The column was washed successively with 100 ml methylene chloride, and 100 ml methylene chloride:methanol (95:5). The fraction which eluted in 95:5 solvent contained about 0.3 g material, and is referred to herein as a 1:1000 extract.

C. The 1:5000 TW Extract

Forty grams of 1:1,000 extract prepared as described above (in scale-up) was concentrated to a small volume in 20 ml acetone. The solution was applied to a 13 cm×14 cm column containing silica gel (800 gm; 60–200 mesh) and eluted with methylene chloride:methanol (97:3) to produce six 1 liter fractions. The yield of dried residue from each fraction was about 5% or 2 grams. Fractions 2–5 were combined and the resulting 8 grams of material are referred to herein as the 1:5000 TW extract.

D. The 1:10,000 TW Extract

The 1:5000 TW extract was then applied to an 8 cm×40 cm column containing silica gel (320 gm; 260–400 mesh) and eluted with methylene chloride:methanol (97:3) to produce five 300 ml fractions. Fractions 2–4, which were yellowish in color, were combined. The solvent was removed by evaporation under vacuum to yield 4 grams of light brown powder, referred to herein as the purified (1:10,000) TW extract.

EXAMPLE 3

Thin-Layer Chromatography of Purified TW Extract

One microgram samples of extracts were applied to a silica gel coated aluminum thin layer chromatography plate (Whatman, catalog #4420 222). The development solvent was hexane:methylene chloride:methanol in volume ratios of 1:1:0.15. Following separation, samples were visualized using an ultraviolet lamp and by application of an aerosol of 0.5% vanillin in $H_2SO_4$-ethanol (4:1).

Figure 2B:
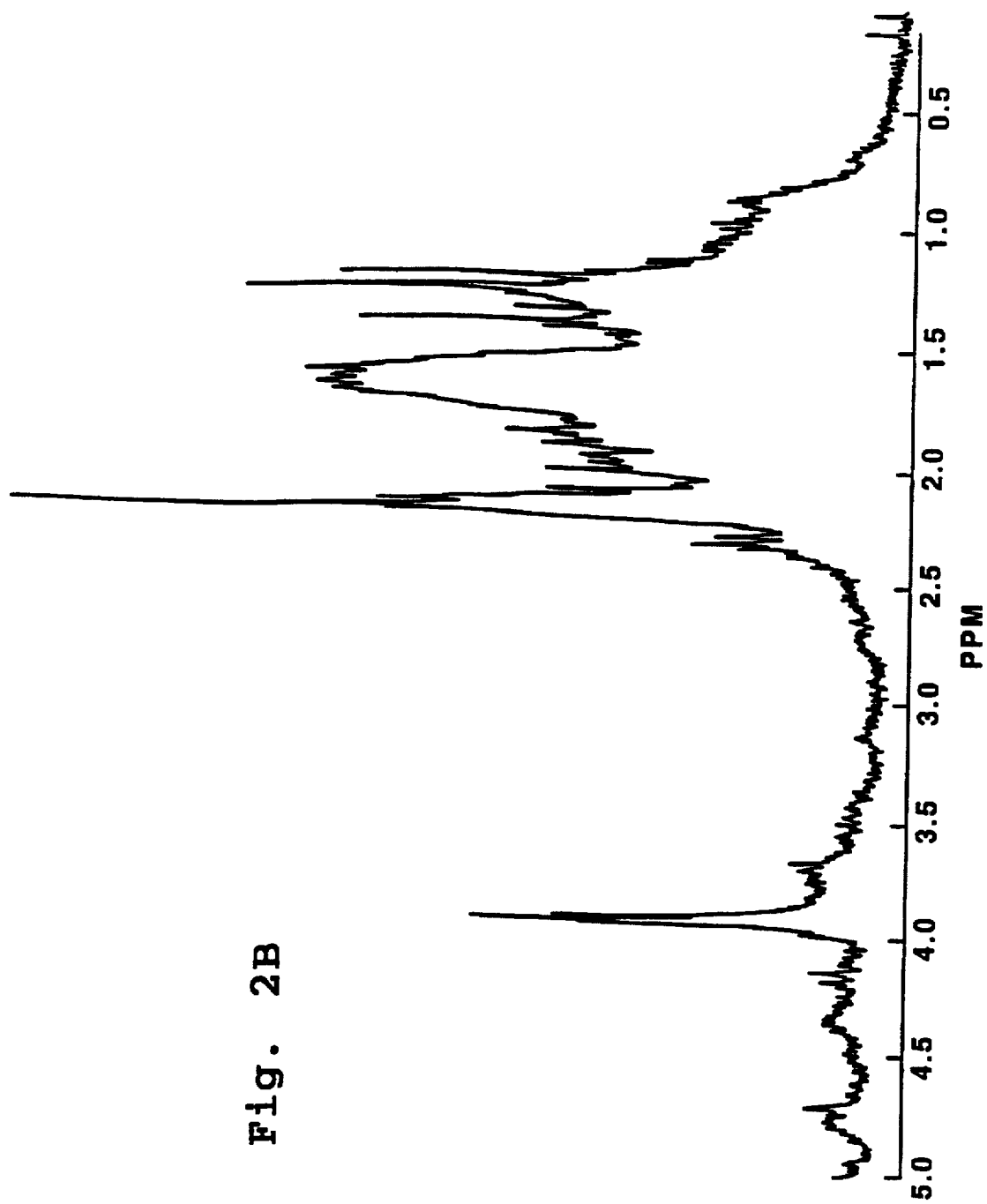
FIG. 2B is a proton NMR spectrum of a purified (1:10000) TW extract.

TLC profiles of the various TW extracts are shown in FIG. 2. Lane A shows the 1:1000 extract, lane B shows the 1:5000 extract and lane C the 1:10,000 extract, herein called the purified TW extract. It can be seen that purification between the 1:1000, 1:5000 and 1:10000 extracts has removed a number of major plant components. For these TW extracts, the thin layer chromatographic profile showed no alkaloid in the extract, as determined by application of the Dragendorff reagent.

EXAMPLE 4

Suppression of Stimulated PBL proliferation in Vitro

Human peripheral blood lymphocytes were prepared using an established method (Boyum, 1968). Human blood buffy coat samples, approximately 40 ml/donor, were obtained from the Stanford University Medical Center Blood Bank. Using sterile technique, the buffy coat samples were gently resuspended in a total volume of 100 ml with the addition of calcium and magnesium free Hank's balanced salt solution (HBSS, obtained from Gibco) at 24° C. A volume of 25 ml of the cell suspension was then layered onto 15 ml of Ficoll-Paque (Pharmacia LKB Biotechnology, Inc.) in a 50 ml conical centrifuge tube. Tubes were centrifuged in a Beckman GPR tabletop centrifuge (GH-3.7 Rotor) at 400×g for 30 minutes at 15° C. with the brake "off" to prevent disruption of the PBL interfaces. Following centrifugation, the PBL interfaces were transferred to new 50 ml tubes using a transfer pipette, and the PBL samples were resuspended in a total volume of 45 ml HBSS and centrifuged at 354×g for 10 minutes at 15° C. with the brake on "low" setting. Supernatants were discarded. PBL's were resuspended in 10 ml HBSS, combined to make a total of 45 ml HBSS, and centrifuged at 265×g for 10 minutes at 15° C. with the brake on "low" setting. The cell pellets were suspended in 10 ml of X-Vivo tissue culture medium (Bio Whittaker) and counted using a hemocytometer. Tissue culture medium was then added to achieve a final cell concentration of $1\times10^6$ cells/ml. Additional dilutions were carried out as required for each assay.

Assays were carried out in 96 well sterile tissue culture plates (Costar 3790, U-bottom and Costar 3595, flat bottom). A volume of 150 μl of X-Vivo medium or sterile distilled water was added to the outer wells of the plate to prevent evaporation of medium within the experimental wells. PBL's from 2 different donors were used in parallel in all experiments. A volume of 100 μl PBL suspension was added to each well using a multichannel pipette. Plates were incubated in an atmosphere of 93% air/7% CO2 in a tissue culture incubator at 37° C. X-35 (AMAC #0178), an anti CD-3 surface antigen antibody was used at 5 ng/ml to stimulate PBL proliferation.

The purified TW extract was diluted in ethanol (10 mg/ml) and then in sterile X-Vivo tissue culture medium to obtain the final concentrations required for each experiment.

After 68 hours total incubation time, 50 μl of X Vivo tissue culture medium containing 8 μCi/ml [$^3$H]-thymidine (Amersham, 49 Ci/mmol) was added to each tissue culture well. Following four hours additional incubation at 37° C., the cells were removed from the tissue culture wells and applied to filter paper using a cell harvester (Brandel). The filter paper was dried for one hour under a heat lamp and then cut into 1 cm discs. Each sample was placed in a scintillation vial containing 2 ml of scintillation fluid (Biosafe, Research products International Corp.). Samples were counted in a Beckman LS 6000SC scintillation counter.

Increasing amounts of purified TW extract produced dose-dependent inhibition of proliferation in both stimulated and unstimulated cells, in a concentration range of 0.3–1.25 μg extract components/ml culture medium. At a concentration of 1.25 μg/ml, the extract reduced unstimulated PBL proliferation 36-fold, and reduced stimulated PBL proliferation 860-fold.

EXAMPLE 5

Effect of Purified TW Extract on Cytokine Production

The ability of the purified *T. wilfordii* extract to affect the production of IL-1, TNF-αa, IL-2, and IL-6, cytokines secreted by anti-CD3 antibody-stimulated (X-35 antibody, 5 ng/ml) and unstimulated human PBLs, was measured.

PBLs were prepared, incubated and treated as described in the preceding example. The purified (1:10,000) TW extract was used at 5 μg/ml. Samples of tissue culture medium were collected at the end of 24 hours incubation and stored at −70° C. prior to assay.

Cytokine measurements were carried out using commercially available ELISA assay kits (R&D Systems), in accordance with the supplier's protocols. In brief, 100 μl of the assay buffer supplied was added to each of the wells of a microtiter plate containing pre-bound anti-cytokine antibody, followed by 100 μl of standard or sample solution, diluted appropriately for the concentration range measured. All incubations were carried out at 37° C. or 24° C. Following two hours incubation, the plates were washed four times with assay buffer, and the second antibody, anti-cytokine labeled with horseradish peroxidase (HRP), was added to each well in a volume of 200 μl. Following a second 2 hour incubation, the wells were washed four times with buffer, and 200 μl of HRP substrate was added to the wells. After 20 minutes incubation, the reaction was terminated by addition of 50 μl $H_2SO_4$ to each well. Optical density was determined using a Molecular Devices microtiter plate reader.

As shown in FIG. 3, basal levels of IL-1, TNFa, IL-2 and IL-6 increased markedly (3.8 to 167 pg/ml, 30.9 to 655 pg/ml, 7.6 to 149 pg/ml, and 109 to 2650 pg/ml, respectively) with X-35 stimulation. At a concentration of 5 μg/ml, the purified TW extract inhibited this X-35 stimulated increase by 16, 89, 93 and 100%, respectively. The extract most likely inhibits cytokine production, though the decrease in medium cytokine concentration could theoretically result from increased catabolism. Decreased cytokine production may be responsible, at least in part, for the decrease in PBL proliferation in vitro and for the immunosuppressive effect of the extract in vivo.

EXAMPLE 6

Cytotoxicity of Extract

Potential cytotoxicity of the purified TW extract (1:10, 000) was assessed by measurement of the extract's effect on the ability of cultured cells to reduce MTT (3-[4,5-Dimethylthiazol-2yl]-2,5-diphenyltetrazolium bromide). MTT, a yellow-colored compound, is reduced by mitochondrial enzymes to form a purple crystalline reduction product (formazan), providing an index of cellular respiration as well as a sensitive assay for cytotoxicity (Green, 1984).

Cytotoxicity was assessed in both cultured PBLs and thymocytes. A stock solution of MTT (Sigma Chemical Co., St. Louis, Mo.), 5 mg MTT/ml phosphate buffered saline, Ph 7.4, was prepared and stored in the dark at 4° C. Following 21 hours incubation under conditions identical to those used in the assays, 25 μl of MTT solution was added to each culture well. After an additional 3-hour incubation, the experiment was terminated by addition of a solution of 10% sodium dodecyl sulfate in 0.01N Hcl. Following overnight incubation at 37° C. (to solubilize the purple crystals, the MTT reduction product), optical density was determined at 570–650 nm in a Molecular Devices microtiter plate reader. Data are expressed as the ratio of the optical density of the extract treated sample to that of untreated controls.

EXAMPLE 7

Treatment of Heart Transplant Rejection

Heterotopic whole heart transplantation was performed according to the standard method (Ono, 1969). The donor (Brown Norway rats, 200–255 g, Charles River, Wilmington, Mass.) and the recipient (Adult male Lewis rats, 225–275 g, Charles River) were anesthetized with sodium pentobarbital (40 mg/kg). Following adequate donor anticoagulation using heparin, the heart graft was removed and stored at 4° C. in PhysioSol Irrigation Solution (Abbott Laboratories, N. Chicago, Ill). The ascending aorta and pulmonary artery were transected, and the vena cava and pulmonary veins were ligated. The recipient abdominal aorta and inferior vena cava were exposed through a median abdominal incision. The donor heart aorta and pulmonary artery were anastomosed end-to-side to recipient's infrarenal abdominal aorta and inferior vena cava, respectively, with running 8-0 monofilament nylon suture (Ethilon, Inc., Somerville, N.J.). Because of the functional properties of the aortic valve, blood did not enter the left ventricle but rather flowed through the coronary arteries to the right atrium, pulmonary artery and the recipient vena cava. The cold ischemic time of all the cardiac grafts was less than 45 minutes. Graft heartbeat was monitored by abdominal palpation. The period of functional graft survival was measured as the number of days during which cardiac graft contractions could be detected by abdominal palpation. Results were confirmed by direct visualization at laparotomy.

A. Treatment with TW Extract

Heart transplant recipient animals prepared as just described (3animals/group) were treated for 14 days with TW extract (1:10,000, 10 mg/kg) or with ethanol solution (5% ethanol, 10 ml/kg), starting on the day prior to surgery and then daily. The TW extract was administered both orally and by intraperitoneal injection. Each heart graft recipient was followed until the graft ceased beating. The results are shown in FIG. 5A, discussed above.

B. Treatment of Allograft Recipient with Cyclosporin/TW Extract Composition

Heart transplant recipient animals prepared as described above (3–10 animals/group) were treated with (i) control solution (5% ethanol, 10ml/kg), (ii) purified (1:10,000) extract (oral administration, 10 mg/kg), (iii) cyclosporin A (intraperitoneal (IP) administration, 0.75 mg/kg), or (iv) cyclosporin A (0.75 mg/kg) in purified extract (1:10,000, 10 mg/kg), administered IP.

The treatment methods started on the day prior to surgery and continuing daily until postoperative day 52, or until the end of allograft survival. Each graft recipient was followed until the graft ceased beating. The results are seen in FIG. 5B, discussed above.

EXAMPLE 8

Treatment of Allograft Rejection with CsA and TW Extract

Heart transplant recipient animals prepared as described in Example 7 were administered intraperitoneally (IP) for 16 days starting one day before transplant with (a) cyclosporin A (CsA) alone at 0.25, 0.5, and 1 mg/kg/day; (b) CsA at 0.12, 0.25, and 0.5 mg/kg/day with TW (1:10,000) ethanol extract at 2.5 mg/kg/day; (c) CsA at 0, 0.25, and 0.5 mg/kg/day with TW (1:10,000) ethanol extract at 5 mg/kg/day; and (d) CsA at 0 and 0.25 mg/kg/day with TW (1:10,000) ethanol extract at 10 mg/kg/day. Survival percentages were recorded 21 days after transplant. The results are shown in FIG. 6.

EXAMPLE 9

Treatment of Heart Xenograft Rejection

Heterotopic whole heart transplantation was performed according to the standard method (Ono, 1969). Donor hearts were obtained from Golden Syrian hamsters, (100–150 g, Charles River Laboratories, Wilmington, Mass). This is a standard model for xenograft transplantation rejection (Wang, 1991; Murase, 1993). The remainder of the procedure was identical to that used in Example 7A, above.

Transplant recipients (3 or 4 animals/group) were treated with (i) control (olive oil, 1 ml/kg), (ii) purified (1:10,000) extract (oral administration, 30 or 60 mg/kg), (iii) cyclosporin A (intraperitoneal administration, 5 or 10 mg/kg), or (iv) cyclosporin A (50 or 10 mg/kg PO) and purified (1:10,000) extract (60 or 30 mg/kg).

The treatment methods started one day prior to transplantation and continued until the time of graft rejection. Each graft recipient was followed until the graft ceased beating. The results are shown in FIGS. 7A and 7B.

EXAMPLE 10

Treatment of Heart Xenograft Rejection With CsA and TW Materials

Heart xenograft recipients prepared as in Example 9(3 to 6 animals/group) were treated with the following treatment regimens:

(a) no drug (control, n=3);
(b) TW extract, 30 mg/kg/day (n=6) until rejection;
(c) CsA, 10 mg/kg/day (n=3) until rejection;
(d) azathioprine, 30 mg/kg/day, plus CsA, 10 mg/kg/day (n=3), for days 1 to 7, 5 mg/kg/day of CsA alone for days 8 to 10*;
(e) tripchlorolide, 0.25 mg/kg/day, plus CsA, 10 mg/kg/day (n=3), for days 1 to 7, 5 mg/kg/day of CsA alone for days 8 to 50; and
(f) triptolide, 0.25 mg/kg/day, plus CsA, 10 mg/kg/day (n=3), for days 1 to 7, 5 mg/kg/day of CsA alone for days 8 to 50.

The results are shown in FIG. 8.

EXAMPLE 11

Effect of Treatment on Anti-Xenograft Antibody Levels

Figure 9A:
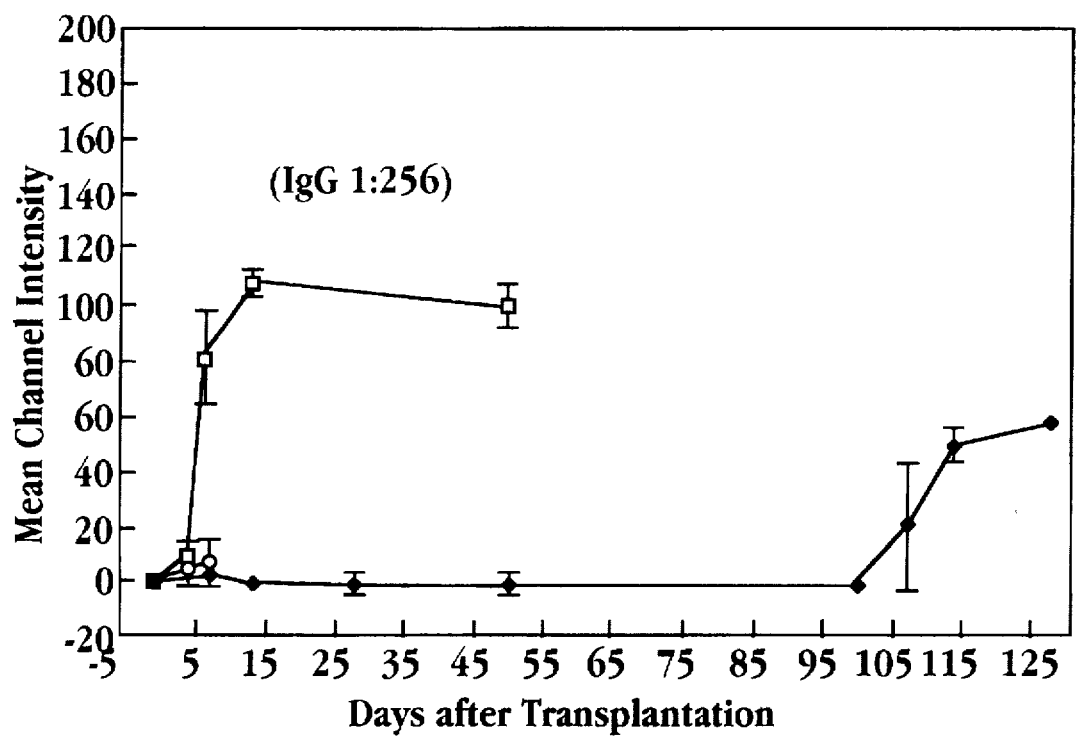
FIGS. 9A and 9B show plots of anti-xenograft IgG (9A) and IgM (9B) levels measured as a function of time in xenograft recipients treated with no drug (control, open squares), TW extract (* symbols), CsA alone (open circles), and TW extract plus CsA (solid diamonds)
Figure 9B:
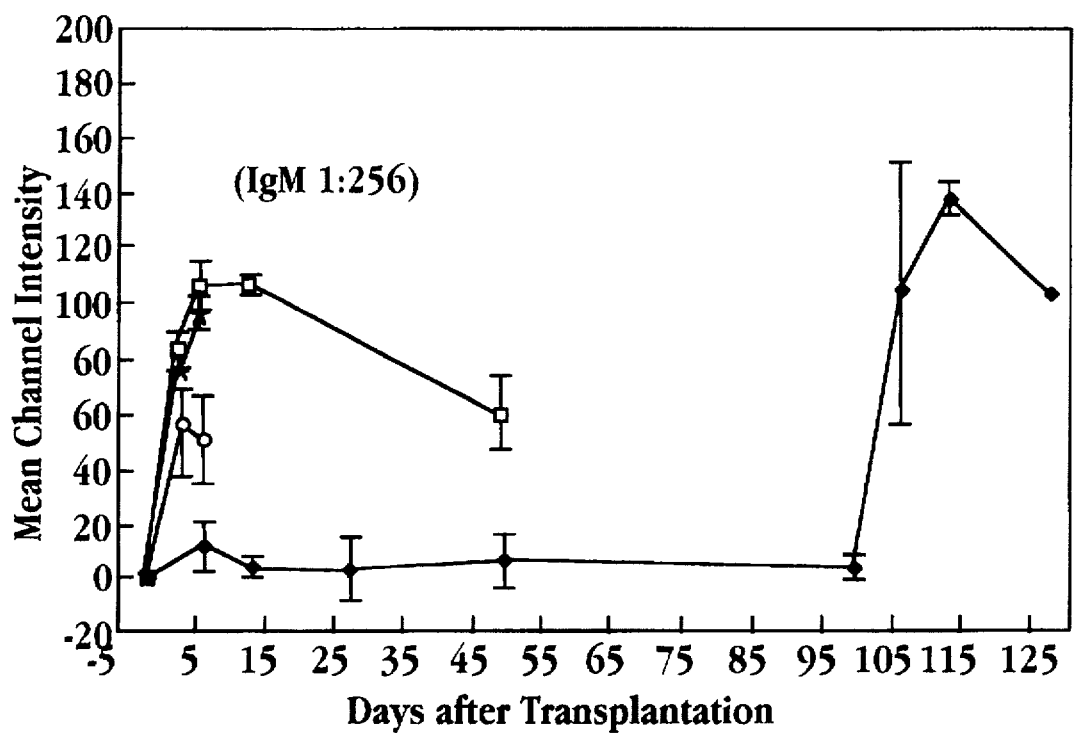

Heart xenograft recipients prepared as in Example 9(3 to 7 animals/group) were treated as indicated below. Lytic antibody titers (IgG and IgM) were measured in the sera of the recipient rats, using hamster red blood cells as targets and baby rabbit serum as a source of complement. Cell lysis was assayed by hemoglobin release into complement fixation diluent as measured with a spectrophotometer (Hasan et al., 1992; Van den Bogaerde et al., 1991). The regimens tested were as follows:

Group A (TW extract study): (a) no drug (control, n=3); (b) TW extract (1:10,000), 30 mg/kg/day (n=6) until rejection; (c) CsA, 10 mg/kg/day (n=3) until rejection; and (d) TW extract (1:10,000), 30 mg/kg/day, plus CsA, 5 mg/kg/day (n=7), for days −1 to 100. The results are shown in FIGS. 9A and 9B.

Group B (tripchlorolide and triptolide study): (a) no drug (control, n=3, from Group A); (b) tripchlorolide, 0.25 mg/kg/day, plus CsA, 10 mg/kg/day (n=3), for days −1 to 7, 5 mg/kg/day of CsA alone for days 8 to 50; and (c) triptolide, 0.25 mg/kg/day, plus CsA, 10 mg/kg/day (n=3), for days −1 to 7, 5 mg/kg/day of CsA alone from day 8 until rejection complete. The results are shown in Figs. 10A and 10B.

EXAMPLE 12

Treatment of Graft-Versus-Host Disease

A. Cell Transplantation in GVHD Mouse Model

C57Bl/6 donor mice (female C57Bl/6 mice, 8–12 weeks of age, from Charles River) were sacrificed, the spleens were removed aseptically, and up to 5 spleens were combined per 15 ml tube containing 10 ml of sterile, HEPES-buffered Hank's balanced salt solution containing 10 percent fetal calf serum (BSS-FCS). Spleens were minced under aseptic conditions in a sterile petri dish using sterile frosted glass slides. Spleens were gently pressed between the frosted ends of the slides to release the splenocytes into the BSS-FCS. The cells were passed through a sterile Pasteur pipette several times to disrupt clumps, and the suspension was then transferred to a sterile 15 ml centrifuge tube. One ml of FCS was placed beneath the cell suspension. The tubes containing the spleen cell suspensions were kept on ice for 5 minutes before either the cell suspensions were transferred to new sterile centrifuge tubes or settled debris and FCS was removed from the bottom of the tube. The cell resultant suspension was mixed gently to assure dispersal.

One ml of FCS was then layered beneath the cell suspension, and the suspension was centrifuged for 10 minutes at 400×g in a refrigerated swinging-bucket centrifuge. The supernatants were aspirated, the pellets diluted to 0.5 ml/spleen in BSS-FCS and combined. Total and viable cell counts were obtained by hemocytometer, using trypan blue dye exclusion, and the cells were suspended at $60 \times 10^6$ viable cells/ml ($30 \times 10^6$ viable cells/mouse). Cell suspensions were kept on ice, and 0.5 ml was administered intravenously to each recipient mouse (female $BDF_1$ mice, 8–12 weeks of age, from Charles River). Controls, including uninjected mice or recipients of $F_1$ splenocytes, were used as appropriate.

B. Assessment of Efficacy of Treatment of GVHD with Extract

The following standard protocol was used. Animals were treated PO daily with 0.1 ml/10 g of body weight of olive oil, olive oil containing 1:10,000 TW extract (30 mg extract/kg/day), or with nothing, for eight days, from the day prior to spleen cell transfer to one day prior to sacrifice.

After the seventh day following transfer, recipient mice were sacrificed and weighed, and spleens were removed and weighed aseptically. The spleens were minced individually under aseptic conditions by rubbing the tissue between sterile frosted glass slides. The cell suspensions were transferred to sterile centrifuge tubes. One ml of FCS was layered beneath the cell suspension and the splenocyte suspensions placed on ice for 5 minutes before discarding debris. One ml of FCS was again layered beneath the cell suspension and the cells were centrifuged for 10 min at 400×g. The cell pellets were resuspended in tissue culture medium (RPMI 1640 containing penicillin, streptomycin, glutamine and sodium pyruvate 10% FCS, 0.5 ml/spleen). Total and viable cell counts were obtained by hemocytometer, using trypan blue dye exclusion, and cells were diluted in tissue culture medium at $10^7$ viable cells/ml. The cells were then cultured for 2 days at 37° C. in an atmosphere in room air containing 5% $CO_2$.

In this assay, inhibition of Con A-stimulated mitogenesis provides a measure of immunosuppression induced by acute GVHD. Drugs or extracts which are active in this assay will prevent or reverse the inhibition, and result in a partially or fully normalized Con A response.

Spleen cells ($10^7$ viable cells/ml, 0.1 ml/microwell, using 96 well tissue culture plates) were incubated in the presence and absence of Con A at 1 ug/ml. After 48 hr, 1 Ci of [$^3$H]-thymidine was added to each well, and the cultures were harvested 18–24 hr later. [$^3$H]-Thymidine incorporation was then measured by liquid scintillation counting, as an index of mitogenesis. The results are shown in FIGS. 11 and 12.

EXAMPLE 13

Transplantation of Bone Marrow and Spleen Cells to Induce GVHD

Standard protocol: Donor female C57Bl/6 mice (8–12 weeks of age, from Charles River) were sacrificed and the spleens and femurs were removed aseptically. Spleens (up to five per tube) were placed in 15 ml tubes containing 10 ml of BSS-FCS. Femurs were pooled in petri dishes containing 10 ml of BSS-FCS and both preparations were kept on ice.

Spleens were minced under aseptic conditions in a sterile petri dish using sterile frosted glass slides and the splenocytes were released into BSS-FCS. The suspension was pipetted though a Pasteur pipette to disrupt clumps and transferred to a sterile 15 ml centrifuge tube.

Both ends of each femur were cut off and the marrow plug was expressed by passing BSS-FCS through the bone shaft with a syringe. Marrow plugs and clumps were dissociated by aspiration and expulsion through a 23 gauge needle. The resultant marrow suspension was apportioned into 15 ml centrifuge tubes (up to 10 femurs per tube), and one ml of FCS was layered beneath the marrow cell suspensions.

Tubes containing spleen or BM cell suspensions were kept on ice for 5 minutes, to allow remaining debris to settle, and then transferred to new sterile centrifuge tubes. One ml of FCS was added beneath each transferred suspension, and the suspensions were then centrifuged for 10 minutes at 400×g in a refrigerated swinging-bucket centrifuge. The pellets were resuspended and pooled in small volumes of BSS-FCS.

The viable and total cell concentrations were determined using trypan blue exclusion and hemocytometer counts, and the cells diluted appropriately (to $120 \times 10^6$ viable spleen cells/ml and $40 \times 10^6$ viable bone marrow cells/ml, which provides $30 \times 10^6$ viable spleen cells and $10 \times 10^6$ viable bone marrow cells per 0.5 ml). Equal volumes of bone marrow and spleen cells were combined to provide a sufficient volume for the intended experiment. An aliquot of bone marrow cells only was prepared for bone marrow (BM) control mice.

Cell suspensions (0.5 ml total volume) were administered intravenously to lethally irradiated (950 cGy of X-irradiation) female $BDF_1$ mice (8–12 weeks of age, from Charles River).

Animals were injected intraperitoneally (IP) with olive oil or olive oil containing TW extract (30 mg/kg body weight) beginning one day prior to bone marrow/spleen cell transfer and continuing daily for a total of 14 doses.

Body weights were recorded daily for objective evaluation of general health. Daily observations of appearance and health were made, to evaluate radiation effects, bone marrow engraftment, GVHD, and infection. Survival data were recorded daily. Effects of drug treatment upon the above parameters were noted. The results are shown in FIG. 13.

Although the invention has been described with respect to particular methods and applications, it will be appreciated that various changes and modifications may be made without departing from the spirit of the invention.

Although the invention has been described with respect to particular methods and applications, it will be appreciated that various changes and modifications may be made without departing from the spirit of the invention.

It is claimed:

1. A method of suppressing xenograft rejection in a host subject, comprising administering to the subject, an immunosuppressant drug selected from the group consisting of cyclosporin A, FK506, azathioprine, rapamycin, mycophenolic acid, a gluco-corticoid, and cyclophosphamide, where the drug or amount of drug administered is, by itself, ineffective to suppress xenograft rejection in the subject, and administering to the subject a potentiator selected from the group consisting of (i) an ethanolic extract of *Triterygium wilfordii* and a (ii) purified triptolide component of said extract, in an amount effective to suppress xenograft rejection in the host in combination with the immunosuppressant drug.

2. The method of claim 1, wherein the immunosuppressive drug is cyclosporin A.

3. The method of claim 2, wherein the potentiator is an ethanolic extract of *Trypterygium wilfordii*.

4. The method of claim 2, wherein the potentiator is a purified triptolide component selected from the group consisting of 16-hydroxytriptolide, triptolide, and tripchlorolide.

5. The method of claim 1, wherein the potentiator is an ethanolic extract of *Trypterygium wilfordii*.

6. The method of claim 1, wherein the potentiator is a purified triptolide component selected from the group consisting of 16-hydroxytriptolide, triptolide, and tripchlorolide.

7. The method of claim 1, wherein said immunosuppressive drug and potentiator are both administered at regular intervals over a time period of at least 2 weeks.

8. The method of claim 1, wherein the amount of immunosuppressant drug administered is between about 20% and 100% of the amount of drug needed to suppress xenograft rejection in the host.

9. The method of claim 1, wherein the immunosuppressant drug and the potentiator are administered parenterally.

10. The method of claim 1, wherein the immunosuppressant drug and the potentiator are administered orally.

* * * * *